(12) United States Patent
Sorenson et al.

(10) Patent No.: US 8,370,079 B2
(45) Date of Patent: Feb. 5, 2013

(54) ALGORITHMS FOR SEQUENCE DETERMINATION

(75) Inventors: Jon Sorenson, Alameda, CA (US); Susan Tang, Los Altos, CA (US); Patrick Marks, San Francisco, CA (US); Chen-Shan Chin, San Leandro, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 394 days.

(21) Appl. No.: 12/592,284

(22) Filed: Nov. 20, 2009

(65) Prior Publication Data

US 2010/0169026 A1 Jul. 1, 2010

Related U.S. Application Data

(60) Provisional application No. 61/116,439, filed on Nov. 20, 2008.

(51) Int. Cl.
*G06F 19/00* (2011.01)
*G06F 19/10* (2011.01)

(52) U.S. Cl. .......................................... 702/20; 702/19

(58) Field of Classification Search ........................ None
See application file for complete search history.

(56) References Cited

U.S. PATENT DOCUMENTS

| | | | |
|---|---|---|---|
| 5,547,839 | A | 8/1996 | Dower |
| 6,210,896 | B1 | 4/2001 | Chan |
| 6,255,083 | B1 | 7/2001 | Williams |
| 6,787,308 | B2 | 9/2004 | Balasubramanian |
| 7,056,661 | B2 | 6/2006 | Korlack et al. |
| 7,085,651 | B2 | 8/2006 | Yasuda |
| 7,406,385 | B2 | 7/2008 | Sorenson |
| 2003/0096253 | A1 | 5/2003 | Nelson |
| 2003/0190647 | A1 | 10/2003 | Odera |
| 2003/0200033 | A1 | 10/2003 | Segal et al. |
| 2003/0215862 | A1 | 11/2003 | Parce |
| 2004/0048300 | A1 | 3/2004 | Sood |
| 2004/0152119 | A1 | 8/2004 | Sood |
| 2004/0224319 | A1 | 11/2004 | Sood |
| 2006/0136144 | A1 | 6/2006 | Kamentsky |
| 2009/0024331 | A1 | 1/2009 | Tomaney |
| 2009/0208961 | A1* | 8/2009 | Bjornson et al. ............. 435/6 |
| 2009/0298075 | A1* | 12/2009 | Travers et al. ............... 435/6 |
| 2010/0160172 | A1* | 6/2010 | Erlich et al. ................ 506/8 |

FOREIGN PATENT DOCUMENTS

| | | |
|---|---|---|
| WO | WO 91/06678 A1 | 5/1991 |
| WO | WO 96/27025 A1 | 9/1996 |
| WO | WO 99/05315 A2 | 2/1999 |

OTHER PUBLICATIONS

Li et al. (Genome Research (2008) vol. 18, pp. 1851-1858; published online on Aug. 19, 2008).*
Ewing et al. (Genome Research (1998) vol. 8, pp. 186-194).*
Mardis et al. (Annu. Rev. Human Genet. (2008) vol. 9, pp. 387-402).*
Shendure and Ji (Nature Biotech. (Oct. 2008) vol. 26; pp. 1135-1145).*
Eddy (Current Opin. In Struct. Biol. (1996) vol. 6, pp. 361-365).*
Altshuler D; Nature. Sep. 28, 2000;407(6803):513-6.
Birney, E. (2001) IBM J. Res. & Dev. 45(3/4):449-454.
Boufounos P., El-Difrawy S., Ehrlich D., "Hidden Markov Models for DNA Sequencing." Proceedings of Workshop on Genomic Signal Processing and Statistics (GENSIPS 2002), Oct. 2002, Raleigh, NC, USA.
Churchill, et al. (1992) Genomics 14: 89-98.
Eid et al., Science 323:133-138 (Jan. 2, 2009).
Hein, J. (1989) Mol. Biol. Evol. 6(6): 649-668.
Levene et al., Science 299 (5607):682-686 (2003).
Rabiner, R.R. (1989) Proceedings of the IEEE; 77(2):257-286.
Stephens, et al. (2006) Nature Genetics 38(3):375-381.
Hertz, G.Z. et al. "Identifying DNA an Proteing Patterns with Statistically Significant Aligments of Multiple Sequences" Bioinformatics (1999) 15(7-8):563-577.
Miller, R.T. et al. "A Comprehensive Approach to Clustering of Expressed Human Gene Sequence: The Sequence Tag Alignment and Consensus Knowledge Base" Genome Res (1999) 9(11):1143-1155.
International Search Report issued Jun. 30, 2010 for corresponding PCT Application PCT/US2009/006224 filed Nov. 20, 2009.
International Report on Patentability issued Jun. 3, 2011 for corresponding PCT Application PCT/US2009/006224 filed Nov. 20, 2009.

* cited by examiner

*Primary Examiner* — Lori A Clow
(74) *Attorney, Agent, or Firm* — Morgan, Lewis & Bockius LLP

(57) ABSTRACT

The present invention is generally directed to powerful and flexible methods and systems for consensus sequence determination from replicate biomolecule sequence data. It is an object of the present invention to improve the accuracy of consensus biomolecule sequence determination from replicate sequence data by providing methods for assimilating replicate sequence into a final consensus sequence more accurately than any one-pass sequence analysis system.

29 Claims, 14 Drawing Sheets

|   | A | B | C | D | E | F | G | H | I |
|---|---|---|---|---|---|---|---|---|---|
| 1 | A | G | T | C | G | – | C | T | T |
| 2 | A | G | – | C | G | – | C | T | T |
| 3 | A | – | – | C | G | – | – | T | T |
| 4 | T | T | T | C | G | C | C | T | T |
| 5 | A | G | T | C | G | – | C | T | T |
| 6 | A | G | – | C | G | – | C | T | T |
| 7 | A | – | – | C | G | – | – | T | T |
| 8 | A | T | T | C | G | C | C | T | T |
| 9 | A | – | – | C | G | – | – | T | T |
| 10 | A | T | T | C | G | C | C | T | T |

Figure 3

ALGORITHMS FOR SEQUENCE DETERMINATION

CROSS-REFERENCE TO RELATED APPLICATIONS

This application claims the benefit of U.S. Provisional Application No. 61/116,439, filed Nov. 20, 2008, the disclosure of which is incorporated herein by reference in its entirety for all purposes.

STATEMENT REGARDING FEDERALLY SPONSORED RESEARCH

Not Applicable.

BACKGROUND OF THE INVENTION

Advances in biomolecule sequence determination, in particular with respect to nucleic acid and protein samples, has revolutionized the fields of cellular and molecular biology. Facilitated by the development of automated sequencing systems, it is now possible to sequence whole genomes. However, the quality of the sequence information must be carefully monitored, and may be compromised by many factors related to the biomolecule itself or the sequencing system used, including the composition of the biomolecule (e.g., base composition of a nucleic acid molecule), experimental and systematic noise, variations in observed signal strength, and differences in reaction efficiencies. As such, processes must be implemented to analyze and improve the quality of the data from such sequencing technologies.

One strategy for improving sequence data is to use redundant sequence data, e.g., as a means to improve accuracy by allowing random errors to be identified and resolved in the final sequence determination. However, the methods currently used are typically restrictive with regards to the types of polymorphisms that may be analyzed and the types of error models that can be used. As such, there is a need for a more powerful and flexible method for consensus sequence determination from redundant biomolecule sequence data.

Various embodiments and components of the present invention employ signal and data analysis techniques that are familiar in a number of technical fields. For clarity of description, details of known analysis techniques are not provided herein. These techniques are discussed in a number of available reference works, such as: R. B. Ash. Real Analysis and Probability. Academic Press, New York, 1972; D. T. Bertsekas and J. N. Tsitsiklis. Introduction to Probability. 2002; K. L. Chung. Markov Chains with Stationary Transition Probabilities, 1967; W. B. Davenport and W. L Root. An Introduction to the Theory of Random Signals and Noise. McGraw-Hill, New York, 1958; S. M. Kay, Fundamentals of Statistical Processing, Vols. 1-2, (Hardcover—1998); Monsoon H. Hayes, Statistical Digital Signal Processing and Modeling, 1996; Introduction to Statistical Signal Processing by R. M. Gray and L. D. Davisson; Modern Spectral Estimation: Theory and Application/Book and Disk (Prentice-Hall Signal Processing Series) by Steven M. Kay (Hardcover—January 1988); Modern Spectral Estimation: Theory and Application by Steven M. Kay (Paperback—March 1999); Spectral Analysis and Filter Theory in Applied Geophysics by Burkhard Buttkus (Hardcover—May 11, 2000); Spectral Analysis for Physical Applications by Donald B. Percival and Andrew T. Walden (Paperback—Jun. 25, 1993); Astronomical Image and Data Analysis (Astronomy and Astrophysics Library) by J. L. Starck and F. Murtagh (Hardcover—Sep. 25, 2006); Spectral Techniques In Proteomics by Daniel S. Sem (Hardcover—Mar. 30, 2007); Exploration and Analysis of DNA Microarray and Protein Array Data (Wiley Series in Probability and Statistics) by Dhammika Amaratunga and Javier Cabrera (Hardcover—Oct. 21, 2003).

BRIEF SUMMARY OF THE INVENTION

The invention is generally directed to processes for analyzing replicate sequence information, and for ultimately identifying a consensus sequence of a biomolecular target sequence from the replicate sequence information. Consequently, the invention is also directed to systems that carry out these processes.

The invention and various specific aspects and embodiments will be better understood with reference to the following detailed descriptions and figures, in which the invention is described in terms of various specific aspects and embodiments. These are provided for purposes of clarity and should not be taken to limit the invention. The invention and aspects thereof may have applications to a variety of types of methods, devices, and systems not specifically disclosed herein.

Furthermore, the functional aspects of the invention that are implemented on a computer or other logic processing systems or circuits, as will be understood to one of ordinary skill in the art, may be implemented or accomplished using any appropriate implementation environment or programming language, such as C, C++, Cobol, Pascal, Java, Javascript, HTML, XML, dHTML, assembly or machine code programming, RTL, etc.

The present invention is generally directed to powerful and flexible methods and systems for consensus sequence determination from replicate biomolecule sequence data. Technologies and methods for biomolecule sequence determination do not always produce sequence data that is perfect. For example, it is often the case that DNA sequencing data does not unambiguously identify every base with 100% accuracy, and this is particularly true when the sequencing data is generated from a single pass, or "read." Using replicate sequence information provides a means to improve validation of sequence reads as compared to single sequence fragment analysis alone. As such, it is an object of the present invention to improve the accuracy of consensus biomolecule sequence determination from replicate sequence data. In certain aspects, the current invention provides algorithms for assimilating replicate sequence into a final consensus sequence more accurately than any one-pass sequence analysis system.

In certain aspects, the methods are computer-implemented methods. In certain aspects, the algorithm and/or results (e.g., consensus sequences generated) are stored on computer-readable medium, and/or displayed on a screen or on a paper print-out. In certain aspects, the results are further analyzed, e.g., to identify genetic variants, to identify a source of the replicate sequence information, to identify genomic regions conserved between individuals or species, to determine relatedness between two individuals, to provide an individual with a diagnosis or prognosis, or to provide a health care professional with information useful for determining an appropriate therapeutic strategy for a patient.

In certain aspects, the invention provides methods of determining a consensus sequence. In certain embodiments, such methods include providing a plurality of replicate sequence reads and aligning those reads to generate a multiple sequence alignment. The multiple sequence alignment (MSA) is analyzed to determine a percent of majority calls for each position in a given region of the MSA and based upon that percent at least one set of sequential positions is identified in that region. In preferred embodiments, each position in the set of sequential positions has a percent of majority calls below a threshold, which can be, e.g., at least 40%, 50%, 60%, 70%, 80%, 95%, 98%, or 99%. Replicate sequence read information for the sequential positions is used in a statistical pattern classification algorithm to generate a consensus sequence spanning the sequential positions, and such information includes but is not limited to calls from the replicate sequence reads for the sequential positions, calls from the replicate sequence reads for the replicate sequence reads, positions adjacent to the sequential positions, call quality metrics, trace features for platform limitation metrics, expected error metrics, details of sequencing technology used to generate the replicate sequence reads, and other nonlocal considerations. In certain preferred embodiments, the consensus sequence is a biomolecular sequence, e.g., a polynucleotide or polypeptide sequence. In certain embodiments, the plurality of replicate sequence reads is provided by performing a sequence-by-incorporation assay, e.g., in a zero-mode waveguide. Various methods for providing the replicate sequence reads include repeatedly sequencing a single molecule or sequencing multiple molecules, each of which comprises at least a portion of the given region. Alignment of the multiple replicate sequence reads generally involves one or more MSA algorithms, e.g., that use a reference sequence or that use a de novo assembly routine. Alignment can further comprise consideration of the read quality and/or call quality for each of the multiple reads, e.g., replicate sequence reads with low read quality and/or low call quality may be excluded from the alignment step. In certain embodiments, the percent of majority calls is determined for each position in the region by dividing a count for a most frequent call at a given position by a total number of replicate sequence reads that comprise the given position.

In certain embodiments, methods of determining a consensus sequence also include generating a path representation of the MSA, e.g., a directed acyclic graph, and the path representation may also be subjected to pruning heuristics. In certain embodiments, the statistical pattern classification algorithm finds a shortest path for calls across the sequential positions, e.g., by applying one or more likelihood models, error models, probabilistic graph models (e.g., an all path probabilistic alignment). In certain embodiments, the statistical pattern classification algorithm generates the consensus sequence by a) maximizing a likelihood based upon the replicate sequence reads, and/or b) using a context dependent alignment model parameter based upon a whole genome multiple sequence alignment. In certain preferred embodiments, the statistical pattern classification algorithm applies a dynamic Bayesian network, e.g., a Hidden Markov Model.

In certain embodiments, methods of determining a consensus sequence also include catenating the consensus sequence generated with majority calls from outside the sequential positions in the region of interest. In certain preferred embodiments, methods of determining a consensus sequence identify multiple sets of sequential positions (e.g., using different thresholds for different sets) and generate multiple consensus sequences for the multiple sets of sequential positions. The multiple consensus sequences can be catenated with majority calls from outside the sequential positions in the region of interest to generate a further consensus sequence for the region. The multiple consensus sequences generated can be ranked, e.g., based on probabilities.

In certain embodiments, methods of determining a consensus sequence are applied iteratively for a given plurality of replicate sequence reads, e.g. using different subsets of reads for different iterations of the methods. Such subsets can be chosen by various criteria, e.g., quality thresholds of varying stringency.

In further aspects of the invention, methods are provided for determining a best call at a position in a sequence. Such methods generally include determining a set of experimental calls at a first position in a plurality of replicate sequences, determining a set of experimental calls at one or more positions adjacent to the first position in the plurality of replicate sequences, and using the results from steps a and b in a statistical pattern classification algorithm to generate a best call for the first position. In yet further aspects of the invention, methods are provided for determining a consensus sequence spanning a given region of interest. Such methods typically include providing a data set comprising a plurality of replicate sequence reads comprising calls for each position in the region of interest, identifying successive positions in the region of interest for which the data set contains at least one ambiguous call, inputting the calls from the successive positions into a statistical pattern classification algorithm to determine a best call at each of the successive positions, and catenating the results with calls from positions in the region of interest that are outside the successive positions, thereby determining a consensus sequence spanning the region of interest.

In preferred embodiments, the methods of the invention are computer-implemented methods, e.g., the statistical pattern classification algorithm can be executed by a computer program. Further, one or more replicate sequence reads, the multiple sequence alignment, the sequential positions, and the consensus sequence can be stored on a computer-readable medium and/or displayed on a screen.

In certain aspects, systems for generating consensus sequences are provided. Such systems generally include computer memory containing an alignment of sequence reads, computer-readable code for applying a pattern classification algorithm to the alignment and generating the consensus sequence, and memory or storing the consensus sequences so generated. Further, those of skill in the art will appreciate that that the systems, methods, and algorithms provided by the invention for determining consensus sequences from replicate sequence reads can be used alone or in combination.

BRIEF DESCRIPTION OF THE DRAWINGS

FIG. 3 provides an illustrative example of a multiple sequence alignment.

DETAILED DESCRIPTION OF THE INVENTION

I. General

Figure 1:
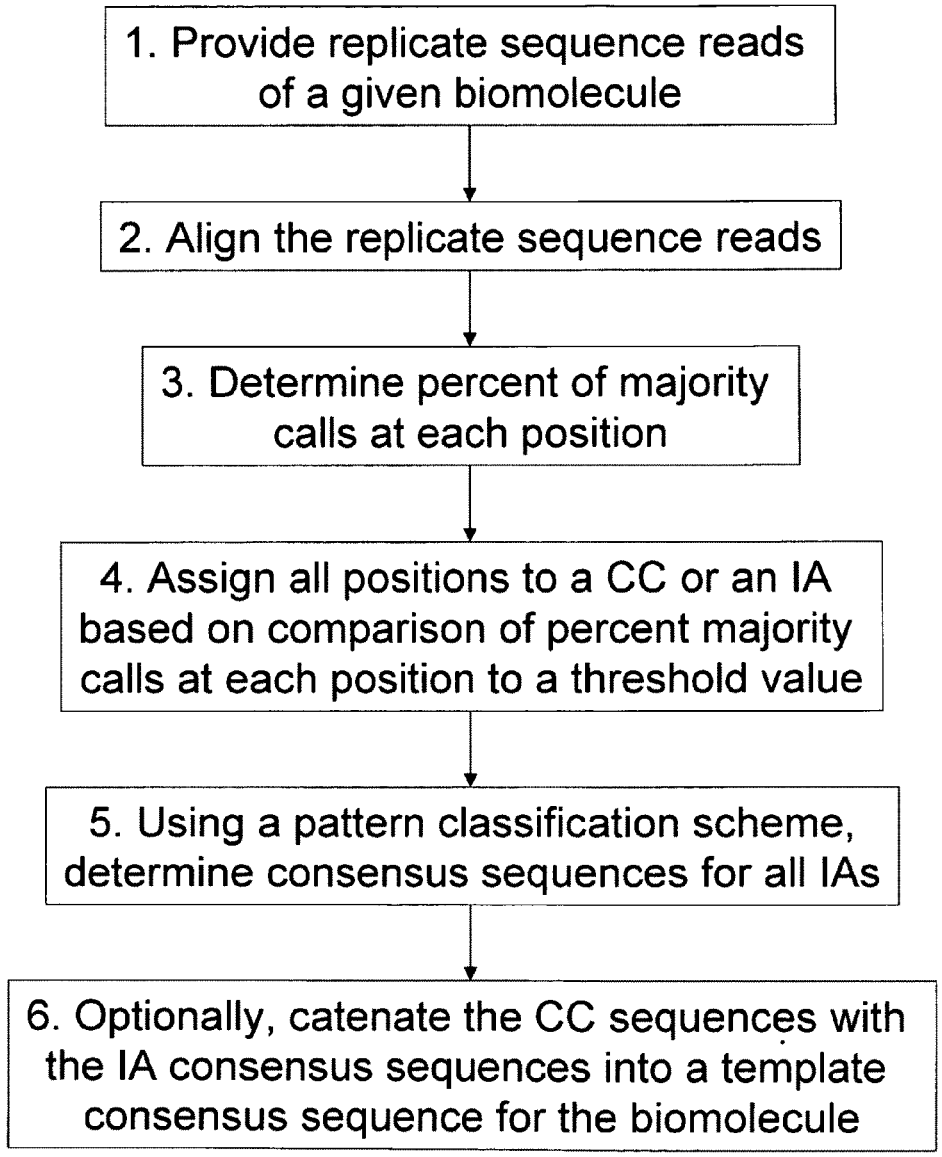
FIG. 1 is a flow diagram providing a general embodiment of the invention.

The present invention is generally directed to powerful and flexible methods and systems for consensus sequence determination from replicate biomolecule sequence data. Technologies and methods for biomolecule sequence determination do not always produce sequence data that is perfect. For example, it is often the case that DNA sequencing data does not unambiguously identify every base with 100% accuracy, and this is particularly true when the sequencing data is generated from a single pass, or "read." Using replicate sequence information provides a means to improve validation of sequence reads as compared to single sequence fragment analysis alone. As such, it is an object of the present invention to improve the accuracy of consensus biomolecule sequence determination from replicate sequence data. In certain aspects, the current invention provides algorithms for assimilating replicate sequence into a final consensus sequence more accurately than any one-pass sequence analysis system.

Previous methods for consensus/variant determination from multiple nucleic acid sequences generally involved analyzing the sequence "calls" and associated quality information at a single position for all reads to determine the base composition for that position, and determining a base identity for each position independently of the determination for every other position. For example, see G. A. Churchill, M. S. Waterman (1992) "The Accuracy of DNA Sequences: Estimating Sequence Quality," *Genomics* 14: 89-98; M. Stephens, et al. (2006) "Automating sequence-based detection and genotyping of SNPs from diploid samples," *Nat. Genet.*, 38: 375-381; Li, et al (2008) "Mapping short DNA sequencing reads and calling variants using mapping quality scores," Genome Research 18(11):1851-8; and Chen, et al. (2007) "PolyScan: An automatic indel and SNP detection approach to the analysis of human resequencing data," Genome Research 17(5):659-666, the disclosures of which are incorporated herein by reference in their entireties for all purposes.

The present invention provides methods for consensus sequence determination that do not follow the traditional methods in which a best call is determined for each position independent of the calls at flanking positions. In contrast, certain aspects of the present invention teach a method for consensus sequence determination that involves determination of a best call for a first position in a target sequence that is dependent on the call for at least one position adjacent to the first position. In certain preferred embodiments, a set of best calls for a set of sequential positions in a target sequence is determined based on statistical analysis of the set of observed calls for all the sequential positions in a single operation.

Certain general aspects of the present invention are discussed in U.S. Patent Publication No. 20090024331, which is incorporated by reference herein in its entirety for all purposes.

The methods for consensus sequence determination provided herein provide various benefits over the methods currently described in the field. In certain aspects, the methods provided herein can more accurately identify a consensus sequence from data containing insertions as deletions, as described in detail below. In further aspects, the greater flexibility of these new methods allows the application of a greater variety of error models than can be used for the traditional position-by-position approach, also described below.

In certain aspects, the methods provided herein comprise identifying regions of a biomolecule for which sequencing data are ambiguous. In certain embodiments, a plurality of regions in a biomolecule for which sequencing data are ambiguous are identified as Islands of Ambiguity (IAs), and these regions are adjacent to other regions of the biomolecule identified as Columns of Certainty (CCs). In certain aspects, a threshold value is used to evaluate the sequence data to determine if a position is within a CC or an IA. In further aspects, ambiguous data for positions identified as within an IA are resolved to generate a consensus sequence for that region. In some preferred embodiments, an error model, likelihood model, probabilistic graph model, and/or pattern classification scheme is used to determine the consensus sequence for at least one IA. In particular embodiments, the methods involve determination of a plurality of consensus sequences for a plurality of IAs identified by analysis of replicate sequencing reads of a biomolecule, e.g., a DNA molecule. Consensus sequences for each IA in a biomolecule may optionally be combined with sequence data for CCs in the biomolecule to generate a template consensus sequence extending across multiple IAs and the intervening CCs, e.g., across a target sequence in the template.

Sequences from various kinds of biomolecules may be analyzed by the methods presented herein, e.g., polynucleotides and polypeptides. The biomolecule may be naturally-occurring or synthetic, and may comprise chemically modified units, e.g., acetylated amino acids, methylated nucleotides, etc. In certain embodiments, the biomolecule is a nucleic acid, such as DNA, RNA, cDNA, or derivatives thereof. In some preferred embodiments, the biomolecule is a genomic DNA molecule. The biomolecule may be derived from any living or once living organism, including but not limited to prokaryote, eukaryote, plant, animal, and virus, as well as synthetic and/or recombinant biomolecules.

For ease of discussion, various aspects of the invention will be described with regards to analysis of polynucleotide sequences, but it is understood that the methods and systems provided herein are not limited to use with polynucleotide sequence data and may be used to determine consensus sequences for other types of biomolecules, e.g., polypeptides.

II. Replicate Sequence Reads

FIG. 1 provides an overview of an exemplary analysis schema for consensus sequence analysis. At step 1, replicate sequence reads are provided for a given biomolecule. Essentially any technology capable of generating sequence data from biomolecules may be used to generate the replicate sequence reads, e.g., Maxam-Gilbert sequencing, chain-termination methods, PCR-based methods, hybridization-based methods, ligase-based methods, microscopy-based techniques, sequencing-by-synthesis (e.g., pyrosequencing, SMRT™ sequencing, nanopore-based methods (e.g., BASE™), etc.). In certain preferred embodiments, the technology used comprises a zero-mode waveguide (ZMW). The fabrication and application of ZMWs in biochemical analysis, and methods for calling bases in sequencing-by-incorporation methods are described, e.g., in U.S. Pat. Nos. 6,917, 726, 7,013,054, 7,056,661, 7,170,050, 7,181,122, and 7,292, 742, and U.S. Patent Publication No. 20090024331, the full disclosures of which are incorporated herein by reference in their entirety for all purposes.

Figure 2:
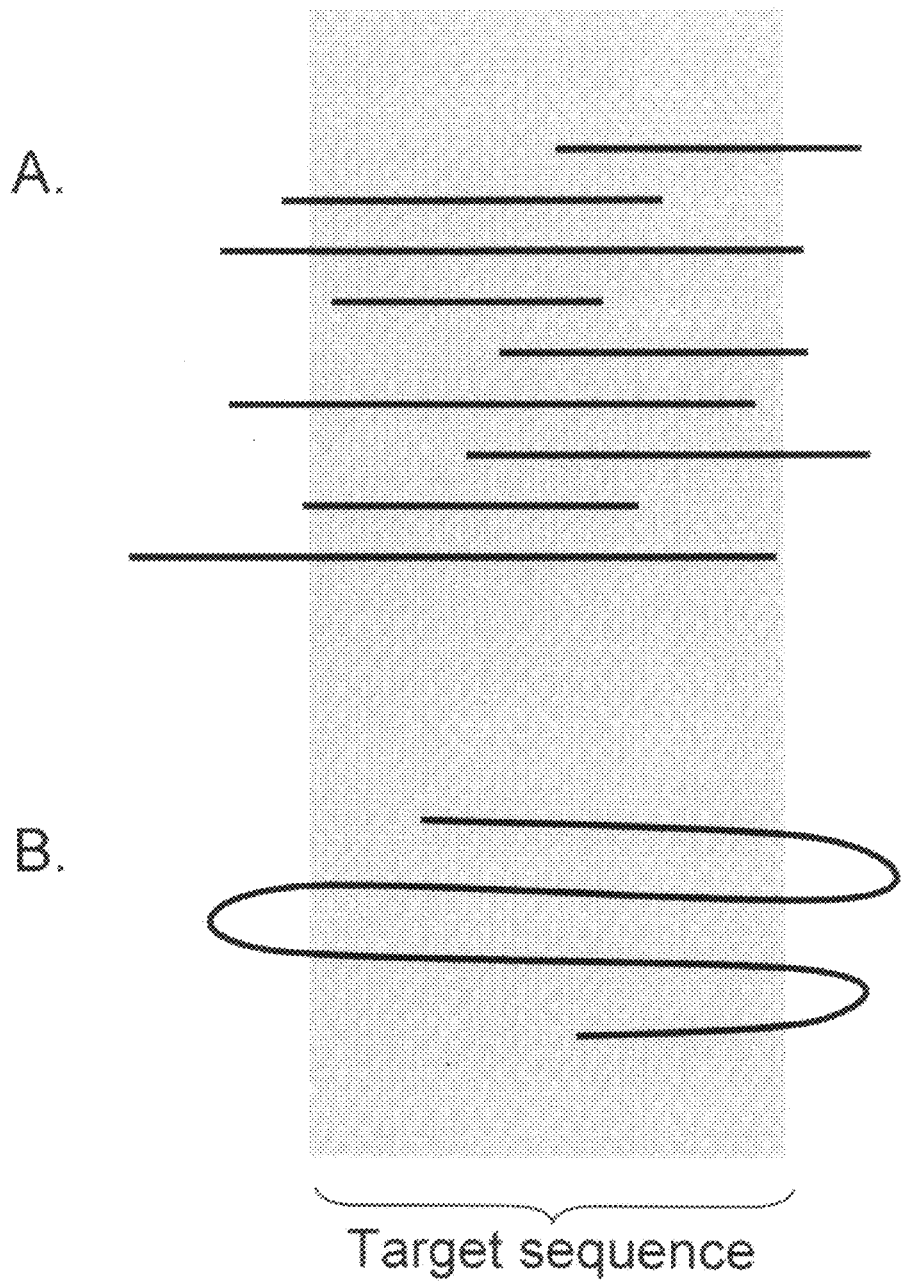
FIG. 2 provides an example of multiple sequence reads that may be used with the methods and systems of the invention.

The multiple sequence reads may be generated in any number of ways, including, e.g., repeatedly sequencing the same molecule, sequencing a template comprising multiple copies of the target sequence, or sequencing multiple individual biomolecules all of which contain the sequence of interest, or "target" sequence. The replicate sequence reads need not begin and end at the same position in the biomolecule sequence, as long as they contain at least a portion of the target sequence, and in some preferred embodiments contain at least a portion of an IA. FIG. 2 provides exemplary replicate sequences. In FIG. 2A, the replicate sequences are from separate sequence reads, e.g., as produced by parallel sequencing strategies. In FIG. 2B, the replicate sequences are contained within a single sequencing read, such as when a circular template is repeatedly sequenced, or when a template contains multiple copies of the target sequence. For example, in certain sequence-by-synthesis applications, such a circular template can be used to generate replicate sequence reads of the target sequence by allowing a polymerase to synthesize a linear concatemer by continuously generating a nascent strand from multiple passes around the template molecule. Examples of methods of generating replicate sequence information from a single molecule are provided, e.g., in U.S. Pat. No. 7,476,503; U.S. Ser. No. 61/099,696, filed Sep. 24, 2008; U.S. Ser. No. 12/413,258, filed Mar. 27, 2009; U.S. Ser. No. 12/413,226, filed Mar. 27, 2009; U.S. Ser. No. 12/531,221; or U.S. Ser. No. 61/094,837, filed Sep. 5, 2008, all of which are assigned to the assignee of the instant application and incorporated herein by reference in their entireties for all purposes. Further, each read may also comprise information in addition to sequence data (e.g., basecalls), such as estimations of per-position accuracy, features of underlying sequencing technology output (e.g., trace characteristics (integrated counts per peak, shape/height/width of peaks, distance to neighboring peaks), signal-to-noise ratios, power-to-noise ratio, signal strength, etc.), and the like.

In certain embodiments, one aspect of the set of replicate sequence reads is that they have been determined to belong together by a previous stage of processing. In other words, the assumption that the set of reads contains replicate sequence data must be validated. In certain embodiments in which the reads are coming from separate single molecules (e.g., as shown in FIG. 2A), a grouping may be necessary to ensure each read in the set contains sequence information for the target sequence of interest. For example, the reads in the set may be identified as covering at least a portion of the Same target sequence by a mapping method, e.g., de novo assembly or alignment to a reference sequence. Such a grouping is not necessary for cases in which the nature of the source of the sequence reads has validated the assumption that the reads belong together, such as cases in which the replicate sequences were generated by sequential sequencing of the same or identical target sequences in a single template molecule to produce a single read containing replicate sequences (e.g., as shown in FIG. 2).

III. Multiple Sequence Alignment

At step 2, the replicate sequence reads are aligned to correlate each call in each read to a given position in the target sequence, thereby generating a "multiple sequence alignment" (MSA). The methods herein may operate with numerous methods for sequence alignment including those generated by various types of known MSA algorithms. For example, the sequence alignment may comprise one or more MSA algorithm-derived alignments that align each read using a reference sequence. In some embodiments in which a reference sequence is known for the region containing the target sequence, the reference sequence can be used to produce an MSA using a variant of the center-star algorithm. Alternatively, the sequence alignment may comprise one or more MSA algorithm-derived alignments that align each read relative to every other read without using a reference sequence ("de novo assembly routines"), e.g., PHRAP, CAP, ClustalW, T-Coffee, AMOS make-consensus, or other dynamic programming MSAs. Depending on the sequence-generating methods used, the determination of sequence alignment may also involve analysis of read quality (e.g., using Trace-Tuner™, Phred, etc.), signal intensity, peak data (e.g., height, width, shape, proximity to neighboring peak(s), etc.), information indicative of the orientation of the read (e.g., 5'→3' designations), clear range identifiers indicative of the usable range of calls in the sequence, and the like. Such read quality may be used to exclude certain low quality reads from the alignment process.

In some embodiments, not every call in each read is used in the alignment process. In some cases, high raw error rates may indicate a benefit to selecting only reads with a high quality (e.g., high certainty). In general, this selection step should not adversely affect the consensus sequence determination process since the subsequent steps do not require that the alignment be correct at every position. As such, various MSA approaches that are well known in the art may be applied. For example, the quality of the calls in each read can be measured and only those identified as "high quality" be used in the alignment process. In some embodiments, a position is not included in the MSA determination if at least a portion of the calls for that position in replicate sequences are below a quality criteria. The quality of a given call is dependent on many factors and is typically closely related to the sequencing technology being used. For example, factors that may be considered in determining the quality of a call include signal-to-noise ratios, power-to-noise ratio, signal strength, trace characteristics, flanking sequence ("sequence context"), and known performance parameters of the sequencing technology, such as conformance variation based on read length. In certain embodiments, the quality measure for the observed call is based, at least in part, on comparisons of metrics for such additional factors to metrics observed during sequencing of known sequences. Methods and software for generating sequence calls and the associated quality information is widely available. For example, PHRED is one example of a base-calling program that also outputs a quality score for each call. After the MSA has been generated, the calls of lower quality may be added back to the alignment, or, optionally may be kept out of the consensus sequence determination process until a later stage.

FIG. 3 illustrates an exemplary polynucleotide multiple sequence alignment (MSA) with ten reads (rows 1-10) and nine nucleotide positions (columns A-I). A nucleotide base call is shown at each position for each read except those positions indicated with a dash "-," which indicates that no call is provided for that position in that read. For example, the call may be indiscernible or of too low a quality to be included in the alignment, or the read may have shown no nucleotide at that position in the template sequence. In some embodiments, dashes are added during the alignment process to allow bases at the same position in a template sequence to align with one another for subsequent analyses.

After the MSA has been generated, the columns in the MSA are classified based on the conformance exhibited by the set of calls at each position. In particular, positions identified as being of "high certainty" are identified based on a particular level of conformance between calls at that position. For example, the calls at a given position for each replicate sequence in the alignment are tallied and compared to identify a majority call (the call most frequently occurring in all reads) and one or more minority calls (calls that are not the majority call). Referring to the example shown in FIG. 3, in column A the majority call is "A" and the minority call is "T," in column B the majority call is "G" and the minority calls are "T" and "-," and so forth. Based on these tallies, a percent of majority calls is determined at each position as the number of sequences in the MSA that contain the majority call at a given position divided by the total number of sequences in the MSA. Referring back to FIG. 3, there are ten sequences in the MSA and the percent majority calls for the positions at column A and column B are therefore 90% and 40%, respectively.

At step 4, the percentages of majority calls for each position determined in step 3 are compared to a threshold value. In certain embodiments, columns that have a percent of majority calls not less than the threshold value are classified as "certain" and are assigned to Columns of Certainty (CCs), while those columns that have a percent of majority calls that is less than the threshold value are assigned to Islands of Ambiguity (IAs). For example, if the threshold is that any position with a percent majority calls not less than 90%, then the positions at columns A, D, E, H, and I in FIG. 3 would be identified as within CCs (shown as shaded in FIG. 3), with percent majority calls at 90%, 100%, 100%, 100%, and 100%, respectively. Likewise, the positions at columns B, C, F, and G would be identified as within IAs with percent majority calls at 40%, 50%, 70%, and 70%, respectively. A $\geq$90% threshold is merely exemplary and other threshold values can be used in the method without departing in spirit and scope of the invention. For example, a threshold may be $\geq$40%, or $\geq$50%, or $\geq$60%, or $\geq$70%, or $\geq$80%, or $\geq$95%, or $\geq$98%, or $\geq$99%. Further, the use of "not less than" versus "less than" with regards to comparing a score to a threshold value is merely a matter of convention, and in alternative embodiments of the present invention the use of "greater than" versus "not greater than" may be used instead, as will be clear to one of ordinary skill in the art.

Determination of a threshold value may be determined, at least in part, on the overall quality of the sequencing reads, the variation or disparity between the reads, the stringency desired by the practioner, etc. It is not necessary that the same threshold be used for every IA in a target sequence, and the determination of an appropriate threshold at each IA may be independently determined. In certain embodiments, the process may be iterated to ensure relative independence from overly relaxed criteria at this stage, and such iterations may use the same or different threshold values. For example, subsequent iterations may increase or decrease the stringency with which the threshold values are determined. Further, the iterations may focus on particular regions of interest within the sample sequences, e.g., particular IAs or CCs or combinations thereof, and need not involve reanalysis of the entire sample sequence.

In certain embodiments, it is determined based on a value that divides the target sequence into CCs and IAs such that a desired fraction (e.g., 50%) of the positions in the target sequence are assigned to IAs. In some embodiments, the same criteria that are used to determine whether the calls in a position are of high enough quality to use for MSA determination are used to determine if a position should be assigned to an IA. In some embodiments, a threshold value is determined based at least in part on ensuring a maximum size for the IAs in a sequence is not exceeded. An IA maximum size may be selected, e.g., based on computational considerations such as the decreasing speed of analysis of increasingly long IAs. After the determination of CCs and IAs, the calls of lower quality that were optionally removed prior to alignment may be added back to the sequences for subsequent steps of the consensus sequence determination process, or, optionally may be kept out until a later stage.

The MSA can be represented as a directed acyclic graph (DAG) that emits all possible sequences given the observed sequences. See, e.g., J. Hein (1989) *Mol. Biol. Evol.,* 6: 649-668. Although path representations of MSAs have been previously used, e.g., for family identification (phylogenetics) and domain classification in protein analysis, the objectives of those studies were consistently focused on using sequences from different sources to determine the differences in biomolecular sequences between such sources. In sharp contrast, the teachings herein provide the insight and know-how to use path representations of MSAs in a fundamentally different way wherein replicate sequences are analyzed for similarities, and those similarities are used to compute consensus sequences of biomolecules.

Figure 4:
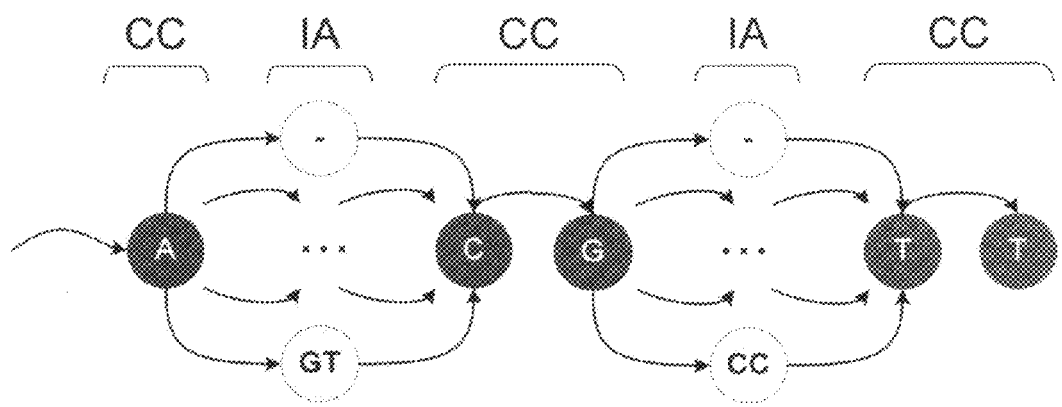
FIG. 4 provides an illustrative example of a directed acyclic graph generated from the multiple sequence alignment depicted in FIG. 3.

In this example, it is approximated that the CCs always emit the sequences they are assigned. FIG. 4 shows a DAG representation of the MSA shown in FIG. 3. The assignment of each node to a CC (articulation point) or IA is indicated. In the IAs, all possible sequences are considered given the observed sequences. At the extreme range of consideration, all 21 sequences that can be formed by a 0-length, 1-length, or 2-length sequence (1+4+16=21) could be considered. Since only a smaller subset of basecalls is observed in this region (G, T), the DAG can be effectively pruned without loss of power. Optionally, possibilities that no one read emits may also be considered. For example, in the possibility of a single T in the first IA may be considered even though no one read only emits a single T in that IA.

In certain embodiments, in particular those with more complex DAGs, it may be prudent to use pruning heuristics to optimize the efficiency of this approach. The number of all possible sequences in an IA is computed by the formula: $(4^{k+1}-1)/3$, where k is the number of positions in the IA. So, for the simple example above, $(4^{2+1}-1)/3=(64-1)/3=21$. However, one can see that as the length of the IA increases there is an exponential scaling of the number of all possible sequences that can be considered. As such, in certain complex applications pruning heuristics will be essential to ensure the computations involved in the consensus sequence determination don't become too cumbersome. Pruning heuristics are well known to those of skill in the art and examples that may be used with the methods and systems described herein include, but are not limited to, greedy algorithms, Monte Carlo methods, branch and bound (BB) algorithm, expectation maximization algorithm, and A* algorithm.

In some embodiments, greedy algorithms are used in consensus sequence determination in the IA. The greedy method is a well-established paradigm that is suited for solving problems which meet the greedy choice property: a global optimum can be readily reached via a series of local improvements from a starting configuration. In this context of work, the objective function is to find the template sequence which will maximize the probability of observing reads spanning the IA. The greedy solution would be to divide into subproblems of increasing template sequence length $\ell$, since the optimal sequence solution for $\ell$=n must contain the optimal sequence solution for $\ell$=n−1 (where n ranges from 1 to the length of the IA). At each stage, find the sequence that yields the highest probability of observing the read set by enumerating only permutations which contain the previous stage's solution. Sequence x is defined to contain sequence y i.f.f. the bases composing y are both present and order-preserved in x. This sub-sampling of template sequence search space results in a significant reduction in computation, especially as the length of individual IA expands.

IV. Consensus Sequence Determination

As noted above, the present invention provides methods for consensus sequence determination that do not follow the traditional methods in which a best call is determined for each position independent of the calls at flanking positions. In contrast, certain aspects of the present invention teach a method for consensus sequence determination that involves determination of a best call for a first position in a target sequence that is dependent on the call for at least one position adjacent to the first position, and in certain preferred embodiments, a best consensus sequence for a set of sequential positions in a target sequence is determined based on statistical analysis of the set of observed calls for the sequential positions. In other words, in certain aspects, this method analyzes a set of ambiguous calls in successive positions in a biomolecule to determine a best consensus sequence spanning the positions, rather than separately analyzing the best call for each position independently of the calls for every other position as in currently known consensus sequence determination methods.

At step 5 in FIG. 1, a pattern classification scheme is used to determine the best consensus sequence for each IA. This statistical analysis can include, for example, a pattern classification scheme that finds a best consensus sequence based on a "shortest path" across the region containing the sequential positions that involves application of a shortest path determination algorithm. For example, a shortest path through a DAG representation of the MSA can be determined, which involves determining the shortest path between any two articulation points. That is, the shortest path across each IA is determined independently of every other IA. Pattern classification schemes for use with the instant invention, including those described above, should preferably be formed based on empirical observation and typically apply a likelihood, error, or probabilistic graph model, or a combination thereof (e.g., classic shortest-path DAG algorithm, Hidden Markov Model, Bayesian networks, kernel methods, nearest-neighbor methods, neural networks, support-vector machines, classification and regression trees (CART), and variations of these). Further, in certain preferred embodiments the model should correlate to the known error in the sequencing methods employed. For example, certain factors can influence the reliability of a SMRT™ sequencing read, e.g., the dyes used, the sequence context, the brightness of the signal, the signal to background ratio, the quality of a particular zero-mode waveguide, and the quality of a particular sequencing instrument. The development and use of such models is generally understood in the art, e.g., see T. Hastie, R. Tibshirani, and J. Friedman (2001) *The Elements of Statistical Learning: Data Mining, Inference, and Prediction*; Springer-Verlag: New York.

To determine a shortest-path across an IA, edge weights are designated for each transition to express the "penalty" of passing from one CC across an adjacent IA to the subsequent CC. Edge weights are generated for each possible path across the IA, and the edge weights should answer the following question: "Given the observed set of reads, what is the likelihood that the template was $\alpha$ where $\alpha$ ranges over the set of possible emissions for each IA. For example, the set of possible emissions for each IA for the exemplary MSA illustrated in FIG. 3 could include: -, G, T, TG, GT, and TT. This likelihood can be computed by an application of Bayes's rule, for example:

$$p(G \mid GT, G, -, TT; prev = A, succ = C) = \frac{p(GT, G, -, TT \mid G; prev = A, succ = C)p(G)}{\sum_\alpha p(GT, G, -, TT \mid \alpha; prev = A, succ = C)p(\alpha)}$$

This formulaic example computes the probability that the template contains only a single G between the "certain" bases A and C in the template, given the observed basecalls of GT, G, -(deletion), and TT. In certain embodiments, such as those in which the reads were generated by SMRT™ sequencing, inclusion of flanking basecalls in the likelihood determination may be useful for identifying spurious signals due to labeled nucleotides that bind to a stalled polymerase, so including these as factors is one way to use the base composition of the template to weight the consensus sequence determination algorithm. The specific formula used may be adjusted by the ordinary practioner depending on the factors in a particular sequence generating system. For example, the above formula may be adjusted to exclude one or both of the flanking basecalls as factors in the computation if they are deemed to not improve the likelihood determinations. Further, the p(G) may be 0.25 if the base composition of the target sequence is unknown, or may be varied if target sequence information provides a more accurate value (e.g., based on the GC content of a reference sequence).

Figure 5:
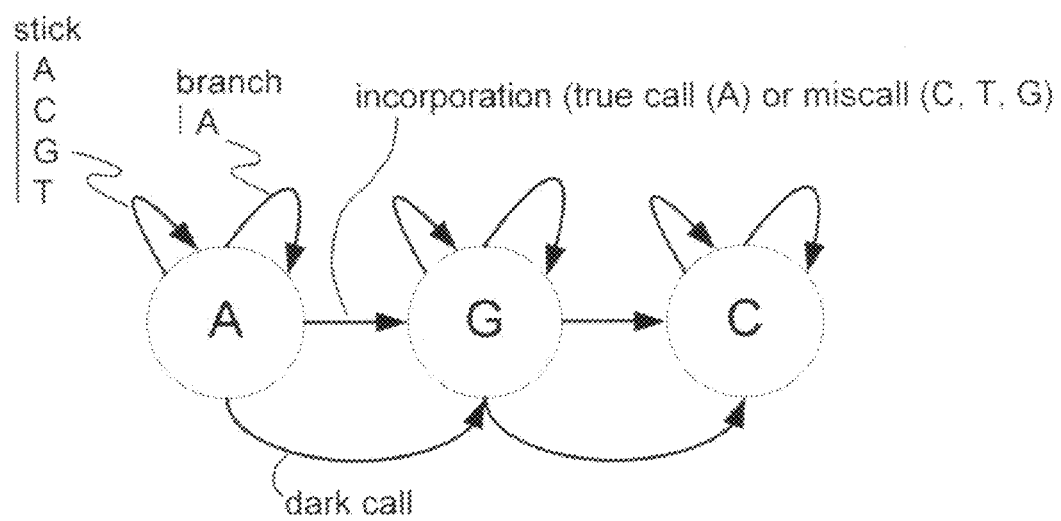
FIG. 5 provides an illustrative example of a "mini-HMM."

Since the denominator is a normalizing constant across all of the edges, the core function to be modeled is the likelihood function: p(GT,G,-,TT|G;prev=A,succ=C), which finds the likelihood of having only a G between the A and C given the observed basecalls. Various models can be constructed to provide the likelihood function. In certain preferred embodiments, the Hidden Markov Model (HMM) is used. In certain embodiments, a "mini-HMM" can be constructed for each likelihood of interest (e.g., for each IA). See, e.g., FIG. 5. Other likelihood functions that could also be used are well known and comprise any general statistical classification algorithm, including, but are not limited to, Gaussian and Poisson processes, maximum likelihood estimations, support vector machine (SVM) likelihoods, neural nets, kernel density estimation, etc. However, this disclosure will focus on the use of HMM likelihood functions. In addition to the specific HMM described herein, more complex HMM approaches are contemplated, e.g. that incorporate models of features related to the sequencing technology generating the replicate reads. For example, trace features (such as peak height, peak spacing, peak width, etc.) may be modeled to provide a "trace-aware" likelihood function.

In certain embodiments, a most likely consensus sequence is discovered for an IA by constructing a series of trial models that maximize the likelihood of the observed data under the model via an expectation maximization procedure. The method is repeated for each IA identified for the set of reads. Once a best consensus sequence is determined for each IA, the graph may be updated by choosing the maximum likelihood paths for each IA to emit the calls for the maximum likelihood sequence.

The use of statistical models for DNA sequencing has been discussed previously. See, e.g., Petros B., et al., "Hidden Markov Models for DNA Sequencing," *Journal of the Franklin Institute*, Vol. 341, Issues 1-2, January-March 2004, pages 23-36, Genomics, Signal Processing, and Statistics. Specifically, Petros discusses HMMs as an approach to DNA basecalling, using techniques such as modeling state emission densities using Artificial Neural Networks, and a modified Baum-Welch re-estimation procedure to perform training. However, they were not discussed as a tool for determining a consensus sequence from replicate sequence information and consensus sequences were only considered to label training data, thus minimizing the need for hand labeling. The use of HMMs for gene prediction and protein family profile analysis is discussed, e.g., in Birney, E. (2001) "Hidden Markov models in biological sequence analysis," *IBM J. Res. & Dev.*, Vol. 45, No. 3/4, but again there is no mention of using HMM analyses to determine consensus sequences for replicate sequence data.

In certain embodiments, a predictive HMM observation distribution model is extended to both the identity of the call and to the features of the signal underlying the call. A likelihood is computed from an HMM using an average model of the HMM parameters (branch, stick, miscall, or dark call) or from parameters dynamically estimated from the data in a previous step and application of the standard Forward algorithm. In brief, the Forward algorithm is a recursive algorithm for calculating $\alpha_t(i)$ for the observation sequence of increasing length t. First, the probabilities for the single-symbol sequence are calculated as a product of initial i-th state probability and emission probability of the given symbol o(1) in the i-th state. Then the recursive formula is applied. Assume $\alpha_t(i)$ has been calculated for some t. To calculate $\alpha_{t+1}(j)$, every $\alpha_t(i)$ is multiplied by the corresponding transition probability from the i-th state to the j-th state, the products are summed over all states, and then the result is multiplied by the emission probability of the symbol o(t+1). Iterating the process, $\alpha_T(i)$ can eventually be calculated, and summed over all states, thereby generating the required probability. See, e.g., Rabiner, L. R. (1989) "A Tutorial on Hidden Markov Models and Selected Applications in Speech Recognition," *Proc. IEEE* 77(2):257-286.

When combining multiple reads of the same DNA into a single consensus read, it is necessary to resolve the ambiguity that exists between reads. A probability model according to specific embodiments of the invention must decide among a number of competing hypotheses about the true target sequence. For example, in attempting to decide between a TA and an AC at a given position the model asks which event is more likely, that a TA base sequence generates an emission that is called as an AC, or that an AC base sequence is called as a TA? While a standard alignment approach of choosing the template that maximizes the likelihood still applies, in the present invention the function that models the probability of an observation is a function not solely of the true calls, but is also extended to return a measure of the probability of observing a signal and various of its associated features on that transition. In this example, if the TA signal has stored or associated with it observed features indicating it was a higher intensity, longer signal (and therefore less likely to be misclassified), while the AC signal was weaker and briefer, these features would be included in the probability model with other alignment probabilities to determine whether TA or AC was more probable. Other features being equal, the probability of having misclassified the bright TA signal being generated from an AC template location would be much smaller than the probability of the weak brief AC signal being generated from a TA base sequence, therefore the model would call TA as the consensus in that position. Because the data analyzed during the consensus alignment phase includes a number of different physical parameters of identified signals and overall reaction parameters, rather than just a single quality score, many different characteristics of a real-time incorporation sequencing reaction can be used in the predictive model. The predictive model can thus be trained to account for the probability that a detected signal was due to a particular event, probabilities of which will vary for different types of biomolecules, as well as account for overall reaction quality features such as overall noise detected at a reaction location or overall confidence of spectral classifications at a reaction location. For example, in the case of SMRT™ sequencing such events can include branches, sticks, miscalls, or "dark" calls. A branch is an event in which a polymerase binds a nucleotide, but unbinds before the incorporation event, resulting in an extra signal being detected for the unincorporated nucleotide. A stick is an event in which a labeled nucleotide sticks to a surface in the detection volume, thereby producing signal in the absence of an incorporation event. The term miscall refers to a minority call at a given position, and a dark call refers to a missing call for a given position. Further illustration of these events is provided in FIG. 5.

In a particular example embodiment, each state of an example HMM models a location along the template DNA strand where the synthesizing polymerase will reside between incorporation events. Two classes of transitions that can occur from this state are (1) a "move" transition where the polymerase incorporates a base and proceeds one position along the template, with a probability denoted by $a_{i,i+1}$ a and (2) a "stay" transition where the polymerase binds a nucleotide, but unbinds before the incorporation event (a "branch") or a labeled nucleotide "sticks" transiently to the surface of the ZMW, inside the illumination region, and the polymerase does not move along the template, with probability given by $a_{i,i}$. A branch generally emits the symbol corresponding to the current template location while a stick generates a random symbol. The probability of branching and sticking are modeled as a function of the observation symbols (A C T G and null), and optionally modeled as a function of symbols for pulse metrics, such as intensity, duration, forward interval, subsequent interval, etc.

There are a variety of potential methods for generating the probability distribution for a multi-dimensional space of signal parameters. Given the various signal parameters and reaction parameters that may be calculated and stored as described herein, one presently preferred approach is to learn the distribution from empirical data acquired from known templates. By aligning the acquired signal stream to the known template, signals from a variety of classes can be used to generate empirical parameter distributions. One method of scoring such a model during training is determining parameters that result in a maximum alignment length as is understood in the art.

In certain embodiments, a most likely consensus sequence is discovered for an IA using a self-consistent statistical pattern classification model that accounts for the local context of the sequence alignment. In certain embodiments, such a model uses a statistical pattern classification algorithm that applies a likelihood model, an error model, or preferably both. For example, such a method can generally comprise two steps: (1) estimation of the context-dependent alignment model parameter using whole genome multiple sequence alignment; and (2) using the estimated model parameters to both determine consensus basecalls and provide a value indicating the discrimination power for each position so basecalled. (The "discrimination power" is defined as the log-odds ratio between the top two calls.) The method is repeated for each IA identified for the set of reads to generate a set of consensus sequences.

In certain preferred embodiments, estimation of the context-dependent alignment model parameters from an MSA preferably is as follows: For a given reference sequence location j in an MSA, the read base count is defined as $n_{j,b}$, where b=A, C, G, T, or "missing" as the number of base b observed in the alignment. The local (2k+1)-mer context is also defined as $C_j = B_{j-k} \ldots B_j \ldots B_{j+k}$, where $B_j$ is the base at location j of the reference sequence and k is a positive integer. The context-dependent base frequencies are defined for all possible (2k+1)-mer c as:

$$f_{c,b} = \frac{\sum_{j, C_j = c} n_{j,b}}{\sum_{b=A,G,C,T} \sum_{j, C_j = c} n_{j,b}}$$

$f_{c,b}$ is considered to be an empirical approximation of the probability to observe a read with base b for given a local sequence context c, and such a probability can be denoted as p(b|c). For example, for the 5-mer context "AACTA" in an exemplary data set, the probabilities are:

$p(A|AACTA) \cong f_{AACTA,A} = 0.0951$ $p(C|AACTA) \cong f_{AACTA,C} = 0.7279$ $p(G|AACTA) \cong f_{AACTA,G} = 0.0461$ $p(T|AACTA) \cong f_{AACTA,T} = 0.0773$ $p(\text{"-"}|AACTA) \cong f_{AACTA,\text{"-"}} = 0.0773$ These probabilities indicate that when a local 5-mer "AACTA" is observed in the reference sequence, about 72.79% of reads at the position aligning to the base "C" are expected to be correctly called as "C." The probability to get a read with "A" (0.0951) is slightly higher than with "G" (0.0461) or "T" (0.0536). Without being bound by theory, in certain cases this difference is caused by the relatively higher number of "A" bases in the 5-mer context, and the probabilities can also be affected by more fundamental biophysical/biochemical processes favoring one base over others at a given context, e.g., depending on characteristics of a sample from which the nucleic acid template was attained. These phenomenological parameters provide useful summary information about the whole system even in the situation where each step including fundamental biophysical, biochemical processes, downstream signal processing and bioinformatics data processing of the system are yet to be fully characterized in a given sequencing system.

As noted above, the estimated model parameters are used to both determine consensus basecalls and provide a value indicating the discrimination power for each position so basecalled. $f_{c,b}$ can be used as the basic parameters of a phenomenological statistical model and to make consensus calls given a multiple sequence alignment. Given that $n_A$, $n_C$, $n_T$ and $n_-$ are the number of reads observed for the bases "A," "C," "G," "T," or missing "-" called at a position j with a local context $C_j$, the four probabilities for the four derived context $C'_{j,b}$ with b=A,C,G, or T can be calculated, where, $C'_{j,b}$ is defined as a new k-mer context replacing the middle base of the with b. The probabilities are calculated using a multinomial distribution model. The base with highest probability is identified as the consensus base called and the log-odds ratio of the top two calls is used as an indication of discrimination power, as follows.

A vector indicating the read base count in a column of the multiple sequence alignment at position j is defined as $n_j = (n_{j,A}, n_{j,C}, n_{j,G}, n_{j,T}, n_{j,-})$. Application of Bayes's rule results in the following equation:

$p(C'_{j,b}|n_j)p(n_j) = p(n_j|C'_{j,b})p(C'_{j,b})$

To compare two hypothesis, $b=b_1$ and $b=b_2$, $b_1, b_1 \in \{A, G, C, T\}$, the log odds ratio is used:

$$E_{j,b_1,b_2} = 10 \log_{10} \frac{p(C'_{j,b_1}|n_j)}{p(C'_{j,b_2}|n_j)}$$

$$= 10 \log_{10} \frac{p(n_j|C'_{j,b_1})}{p(n_j|C'_{j,b_2})} + S,$$

where $$S = 10 \log_{10} \frac{P(C'_{j,b_1})}{P(C'_{j,b_2})}.$$

$p(n_j|C'_{j,b_1})$ and $p(n_j|C'_{j,b_2})$ are calculated using the multinomial distribution, $$p(n_j|C'_{j,b}) = \frac{(n_{j,A} + n_{j,C} + n_{j,G} + n_{j,T} + n_{j,-})!}{n_{j,A}! n_{j,C}! n_{j,G}! n_{j,T}! n_{j,-}!} \prod_{b'=A,C,G,T,-} \left(f_{C'_{j,b},b'}\right)^{n_{b'}}.$$

to generate $$E_{j,b_1,b_2} = 10 \log_{10} \frac{\prod_{b'=A,C,G,T,-} \left(f_{C'_{j,b_1},b'}\right)^{n_{b'}}}{\prod_{b'=A,C,G,T,-} \left(f_{C'_{j,b_2},b'}\right)^{n_{b'}}} + S.$$

Assuming $$\frac{P(C'_{j,b_1})}{P(C'_{j,b_2})} \approx 1, \quad E_{j,b_1,b_2}$$

can be approximated as $$E_{j,b_1,b_2} \approx 10 \log_{10} \frac{\prod_{b'=A,C,G,T,-} \left(f_{C'_{j,b_1},b'}\right)^{n_{b'}}}{\prod_{b'=A,C,G,T,-} \left(f_{C'_{j,b_1},b'}\right)^{n_{b'}}}.$$

The consensus call for the base at position j is made using the mostly likely base by calculating $E_{j,b_1,b_2}$ with all possible combination of $b_1$ and $b_2$. An actual implementation of this method is provided in Example II.

The above method using a self-consistent statistical pattern classification model that accounts for the local context of the sequence alignment does not take into account cases in which the sequence reads in the MSA contain insertions and/or deletions. Further, it uses the simplest assumption about the prior probability. Cases in which sequence reads comprise insertions and/or deletions can be addressed by looking at the aligned position with insertions and deletions. Parameters can also be derived for insertions and deletions by introducing them in silico with some modifications of the reference sequence when building the multiple sequence alignment. Further, a more physical model (e.g. a Hidden Markov Model-based modeling) can be used to derive the context-dependent base frequencies and the prior ratio This method is generally independent of the alignment algorithm used to generate the MSA. Consistent results are expected as long as the context-dependent base frequencies and the base calling and discrimination power calculation use the same sequence alignment procedure. Further, this method as described above does not consider from which strand a basecall is being generated (e.g., forward or reverse), but it will be clear to one of ordinary skill in the art that the model can be extended to do so by known statistical methods. Likewise, the method can be extended for genotype calling where multiple samples are mixed in sequencing, e.g., using a binomial model previously described for genotype calling for short read technology (see, e.g., Li, et al. (2008) Genome Research 18:1851-1858, incorporated herein by reference in its entirety for all purposes). To apply a similar method for genotype calling for longer read sequencing technologies, a context-depending model as presented above increases both sensitivity and specificity.

In yet further embodiments, a most likely consensus sequence is discovered for an IA using a method that takes into consideration the error mode of a given sequencing technology and uses a dynamic programming strategy to simultaneously evaluate all possible consensus sequences for an IA. In certain embodiments, such a method uses a statistical pattern classification algorithm that applies a likelihood model, an error model, a probabilistic graph model, or preferably two or three of these models. The method is repeated for each IA identified for the set of reads to generate a set of consensus sequences.

In certain embodiments, such a method is a recursive relation similar to the HMM method described supra, with the variations that the same dynamic programming strategy is used to evaluate all possible template sequences and a likelihood or alignment score is used to construct the consensus sequence or make the consensus basecalls. In preferred embodiments, such a method uses a variant of a standard alignment algorithm in a nontraditional manner. Rather than using it to identify similarities between two sequences, the alignment algorithm is used to infer a common sequence given a number of noisy observations of the common sequence from the sequencing operation. Such an inference can be described with the following equation:

$$\hat{T} = \max_T P(T \mid r_1 r_2 \ldots r_n; H),$$

where T is the potential template sequence, $r_1 r_2 \ldots r_n$ are the observed reads from 1 to n, and H indicates the error model of the system. The consensus sequence $\hat{T}$ is simply the T such that it maximizes the conditional probability $P(T \mid r_1 r_2 \ldots r_n; H)$.

The conditional probability can be rewritten using Bayes's Rule:

$$P(T \mid r_1 r_2 \ldots r_n; H) = \frac{P(r_1 r_2 \ldots r_n \mid T, H) P(T)}{P(r_1 r_2 \ldots r_n \mid H)}$$

Using a general inference framework, $\hat{T}$ can be found by maximizing the likelihood $P(r_1 r_2 \ldots r_n \mid T, H)$ by evaluation of all possible T.

Figure 10:
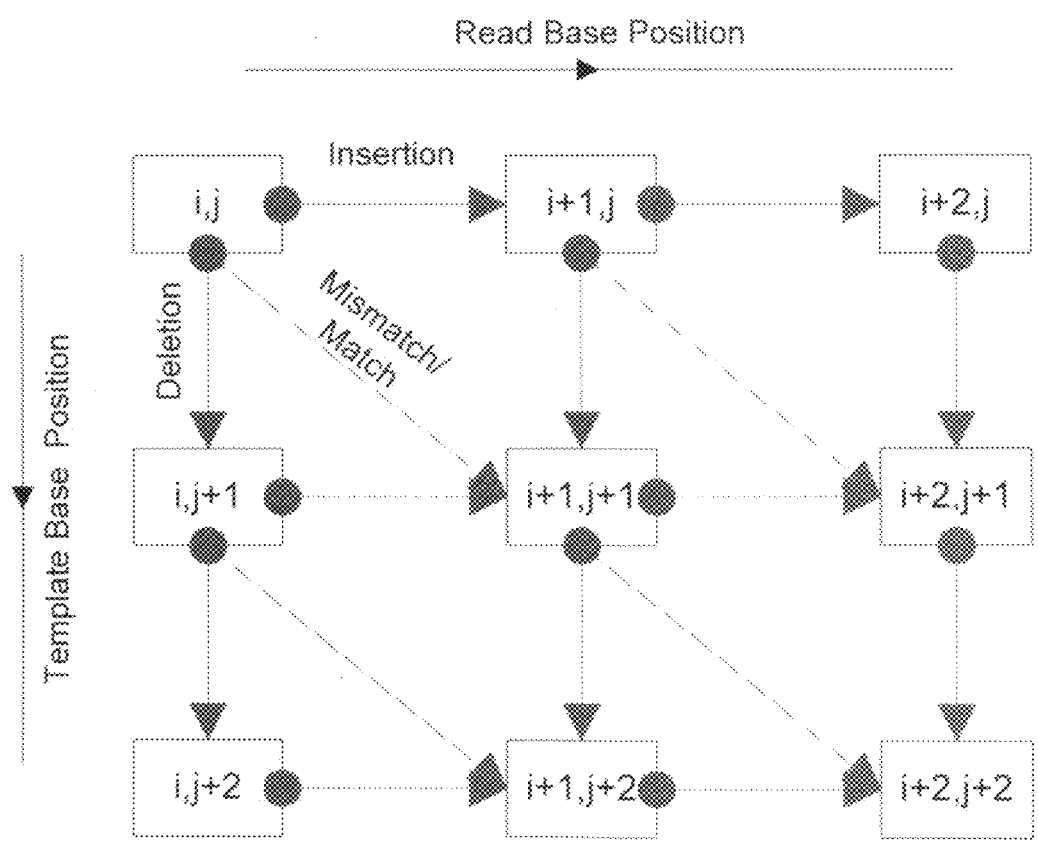
FIG. 10 provides a graphical representation of an alignment lattice.
Figure 11:
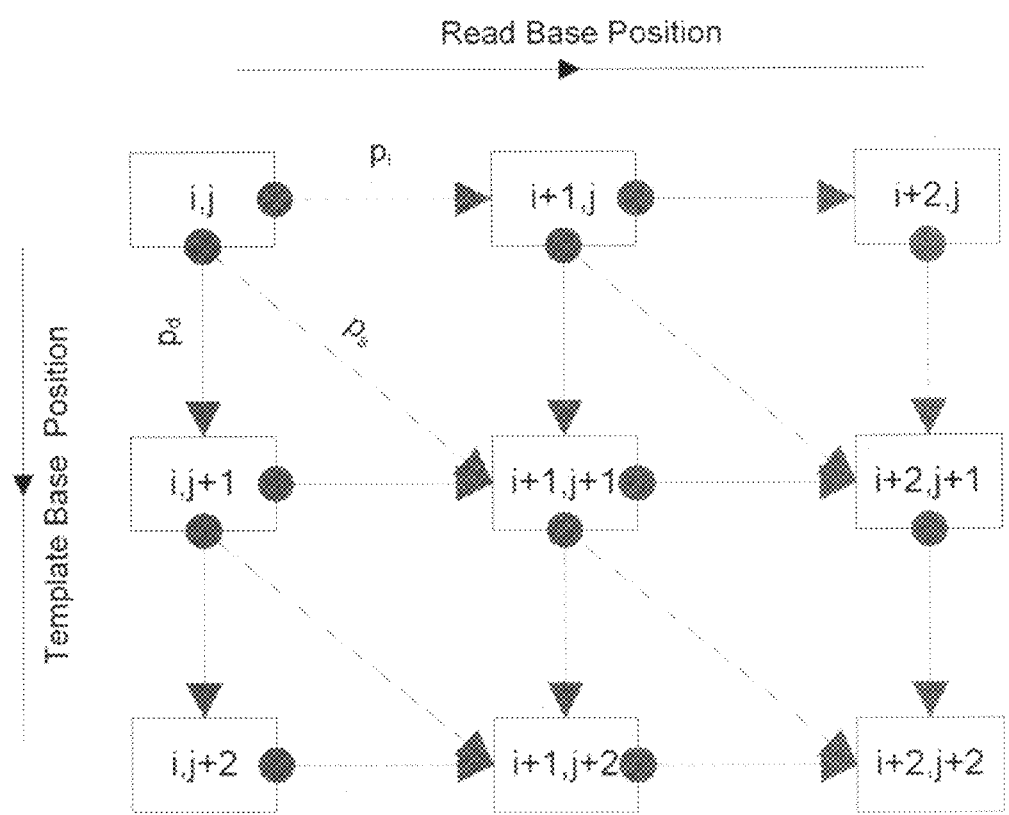
FIG. 11 provides a graphical representation of the probability associated with the alignment lattice shown in FIG. 10.

Various methods can be used to approximate the likelihood function efficiently. In certain embodiments, it is assumed that given a position j in the template, the probability of the observed base calls output by the sequencing methodology is known. Such a probability can be specified, in its most general form, by three probability matrices:

$$p_S(b \in \{A,C,G,T\} \mid t \in \{A,C,G,T\})$$

$$p_I(b \in \{A,C,G,T\} \mid t \in \{A,C,G,T\})$$

$$p_D(b = \text{'-'} \mid t \in \{A,C,G,T\}),$$

where $p_s$ is the substitution probability, and $p_i$ is the insertion probability and $p_d$ is the deletion probability. These three different probability matrices indicate three different ways a base (or a missing event) in the raw read position i is generated at a given template position j. A graphical representation of an alignment lattice is shown in FIG. 10, and a graphical representation of the probability associated with the alignment lattice is shown in FIG. 11.

Using the probability matrices, this probability can be calculated as $$P(r_1, i, j \mid T, H) = \sum_{a \in A_{ij}} P_{path}(a \mid T, H),$$

where $A_{ij}$ is the set of all directed path end at (i,j). The probability, $P(r_1, i, j \mid T, H)$, indicates the i-th base read is generated by the j-th base or no base between i-th and (i+1)-th base in the read is generated by the j-th base in the template for all possible paths. For a given T, $P(r_1, i, j \mid T, H)$ can be calculated for all i and j using a recursive relation.

The following sum of likelihood:

$$P(r_1, i, j, t_{ij} \in \{A, C, G, T\} \mid H) = \sum_{\text{all } T \text{ end with } t_{ij}} P(r_1, i, j \mid T, H),$$

can be calculated by observing the following recursive relation:

$$P(r_1, i, j, t_{ij} \mid H) = \sum_{t_{i-1,j} \in \{A,C,G,T\}} p_I(b_{i-1} \mid t_{i-1,j})$$

$$P(r_1, i-1, j, t_{i-1,j} \mid H) +$$

$$\sum_{t_{i-1,j-1} \in \{A,C,G,T\}} p_S(b_{i-1} \mid t_{i-1,j-1})$$

$$P(r_1, i-1, j-1, t_{i-1,j-1} \mid H) +$$

$$\sum_{t_{i,j-1} \in \{A,C,G,T\}} p_D(\text{'-'} \mid t_{i,j-1})$$

$$P(r_1, i, j-1, t_{i,j-1} \mid H)$$

with the initial condition:

$P(r_1,0,0,t_{00}=A|H)=$ $P(r_1,0,0,t_{00}=C|H)=$ $P(r_1,0,0,t_{00}=G|H)=$ $P(r_1,0,0,t_{00}=T|H)=\frac{1}{4}$ Similarly, the recursive relation can be used to calculate the probability summing over all paths starting at (i,j).

$$F(r_1, i, j, t_{i,j} \mid H) =$$

$$\max \left\{ \begin{array}{l} M_I(b_{i-1} \mid t_{i-1,j}) + F(r_1, i-1, j, t_{i-1,j} \mid H) \mid t_{i-1,j} \in \{A, C, G, T\}, \\ M_S(b_{i-1} \mid t_{i-1,j}) + F(r_1, i-1, j-1, t_{i-1,j} \mid H) \mid t_{i-1,j-1} \in \{A, C, G, T\}, \\ M_D('-' \mid t_{i,j-1}) + F(r_1, i, j-1, t_{i,j-1} \mid H) \mid t_{i,j-1} \in \{A, C, G, T\} \end{array} \right\},$$

and $$B(r_1, i, j, t_{i,j} \mid H) =$$

$$\max \left\{ \begin{array}{l} M_I(b_{i+1} \mid t_{i+1,j}) + B(r_1, i+1, j, t_{i+1,j} \mid H) \mid t_{i+1,j} \in \{A, C, G, T\}, \\ M_S(b_{i+1} \mid t_{i+1,j+1}) + B(r_1, i+1, j+1, t_{i+1,j+1} \mid H) \mid t_{i+1,j+1} \in \{A, C, G, T\}, \\ M_D('-' \mid t_{i,j+1}) + B(r_1, i, j+1, t_{i,j+1} \mid H) \mid t_{i,j+1} \in \{A, C, G, T\} \end{array} \right\}.$$

$$Q(r_1, i, j, t_{ij} \mid H) = \sum_{t_{i+1,j} \in \{A,C,G,T\}} p_I(b_{i+1} \mid t_{i+1,j})$$

$$Q(r_1, i+1, j, t_{i+1,j} \mid H) +$$

$$\sum_{t_{i+1,j+1} \in \{A,C,G,T\}} p_S(b_{i+1} \mid t_{i+1,j+1})$$

$$Q(r_1, i+1, j+1, t_{i+1,j+1} \mid H) +$$

$$\sum_{t_{i,j+1} \in \{A,C,G,T\}} p_D('-' \mid t_{i,j+1})$$

$$Q(r_1, i, j+1, t_{i,j+1} \mid H)$$

with the initial condition:

$Q(r_1,m+1,n+1,t_{m+1,n+1}=A|H)=$ $Q(r_1,m+1,n+1,t_{m+1,n+1}=C|H)=$ $Q(r_1,m+1,n+1,t_{m+1,n+1}=G|H)=$ $Q(r_1,m+1,n+1,t_{m+1,n+1}=T|H)=\frac{1}{4}$ where m is the length of the read and the n is a given parameter that indicates the total length of the template.

The most likely jth base in the template can be inferred by finding which base, A, C, G, and T maximize the following likelihood: most likely template base at $$j = \operatorname*{argmax}_b \sum_i P(r_1, i, j, t_{i,j} = b \mid H) Q(r_1, i, j, t_{i,j} = b \mid H).$$

The number of reads=n for consensus calling. P and Q for each read can be calculated and the consensus base call determined: most likely template base at $$j = \operatorname*{argmax}_b \sum_n \sum_i P(r_n, i, j, t_{i,j} = b \mid H) Q(r_1, i, j, t_{i,j} = b \mid H).$$

The formulation presented here can be formatted as dynamic programming for searching for the best score. Instead of using probability, an alignment score can be assigned for each i,j and $t_{i,j}$. The $p_S$, $p_I$, and $p_D$ are replaced with alignment score matrix: $M_S$, $M_I$, and $M_D$. The recursive relation for P and Q are replaced by:

The most likely consensus basecall in this case is found by the following equation: most likely template base at $$j = \operatorname*{argmax}_b \sum_n \sum_i F(r_n, i, j, t_{i,j} = b \mid H) + B(r_n, i, j, t_{i,j} = b \mid H).$$

If there is a known template sequence, the above formulation can also be used to do consensus SNP calling. By fixing $t_{i,j}=T_j$, where $T_j$ is the template base at position j, for all j except the position with a potential SNP, the SNP can be called using the above formula.

Even when the template sequence is unknown, e.g., for de novo consensus sequence determination, the length of the template sequence must still be specified. The template length can be inferred by maximizing the likelihood for different template lengths, from sample preparation, or using adapter sequence alignment to constrain the length.

The equation presented for the final consensus calling does not use the prior information P(T). If such information is available, a full Bayesian posterior probability can be performed, which in principle can lead to a better inference if the prior information is "more accurate." Further, the choice of $P_S$, $P_I$, $P_D$, $M_S$, $M_I$, and $M_D$ will affect the final performance. As such, in some embodiments a full Hidden Markov Model training algorithm is used to learn the best P's and M's for use in the consensus basecalling algorithm.

Modifications to the methods described above that take into consideration the error mode of a given sequencing technology and use a dynamic programming strategy to simultaneously evaluate all possible consensus sequences for an IA are also contemplated for use with the methods described herein. For example, in certain embodiments, the method comprises assigning the confidence values using an all path probabilistic alignment, which does not require assignment of basecalls to fixed reference template positions as does the method described above. An actual implementation of such a method is provided in Example III.

Specifically, for each of the four possible bases ("A", "C", "G", and "T") at each template position, the confidence values from each read at a given location are summed. The summed confidence values are defined as the consensus confidence values, and are correlated with empirical Phred-style empirical quality values (EQV). The number of bases in the test data set that are still retained after application of the quality filter is determined, and this number is compared with the empirical quality value derived using fold-coverage as the binning method for deriving the EQV.

The 4 possible SNP candidates at each locus are constructed by replacing the base of the original putative template sequence at the given location to the four possible bases "A", "C", "G" and "T", denoted as "$T_{A,i}$," "$T_{C,i}$," "$T_{G,i}$," and "$T_{T,i}$," respectively. Probabilistic alignments were chosen rather than maximum score alignment like the standard Smith-Waterman algorithm because probabilistic alignments can naturally assign the likelihood, $P(r_1 r_2 \ldots r_n | T_b, H)$, for each of the candidates b$\in \{A, C, G, T\}$. The base that gives the greatest likelihood $P(r_1 r_2 \ldots r_n | T_b, H)$, is called as the consensus base call. Furthermore, the log likelihood ratio, $\kappa \equiv \log(P(r_1 r_2 \ldots r_n | T_{b\ max}, H)/P(r_1 r_2 \ldots r_n | T_{b\ 2nd}, H))$, between the best candidate $b_{max}$ to the second best candidate $b_{2nd}$, is used to assess the confidence of the quality of the consensus call. If the likelihood ratio kappa is close to zero, where the best call and the second best call are equally likely, either may be the correct template base. When kappa is large, the alternative possibility that the second best call rather than the best one is the true underlying template base becomes less likely. In this case, the best call is more likely to be the correct one without ambiguity. To use δ (kappa) to predict consensus call quality, the kappa is calculated for all reads at all positions of a sequencing data set where the template sequences are known. The data is binned with every 2% quantiles and the number of errors of the consensus call at each quantile is calculated. For each bin, the phred-style quality value defined as qv=−10 $\log_{10}$ (number of base call errors/total number of base calls) can be calculated. The quality value of the consensus call as function of kappa is then defined as qv=qv($\kappa$), which can be used to predict the error for other independent experimental data sets.

The consensus confidence values defined according to this method are a better predictor of the final quality of the consensus sequence, and are particularly useful for asynchronous DNA sequencing, such as that produced by single-molecule DNA sequencing technologies (e.g., SMRT™ real-time sequencing). In addition, the method can be further modified to explicitly treat the variation of errors due to local sequence context and the raw sequence features (e.g. pulse widths, pulse timing, etc.) by methods that will be apparent to one of ordinary skill based upon the teachings provided herein, e.g., by using an alignment program that accounts for these variabilities.

At step 6, the consensus sequences for each IA are optionally catenated with the majority calls for the CCs to generate a best consensus sequence for the biomolecule. The probabilities generated for each best consensus sequence at each IA can be used to compute a global probability estimate for the final consensus target sequence. Another beneficial result of this decomposition of the target sequence is the generation of a family of consensus sequences for each IA that includes the global probability estimates for each consensus sequence in the family. Such a representation might be useful for preserving information about ambiguities for downstream steps. For example, a family of consensus sequences could be determined and later disambiguated by comparison to additional sequencing data.

V. Computer Implementation

In certain aspects, the methods provided herein are computer-implemented methods, wherein at least one or more steps of the method are carried out by a computer program. In some embodiments, the methods provided herein are implemented in a computer program stored on computer-readable media, such as the hard drive of a standard computer. For example, a computer program for determining at least one consensus sequence from replicate sequence reads can include one or more of the following: code for providing or receiving the replicate sequence reads, code for grouping replicate sequence reads, code for analyzing call quality, code for aligning the replicate sequence reads to generate an MSA, code for determining a percent majority calls at positions in the MSA, code for converting or displaying the MSA as a directed acyclic graph, code for identifying IAs, code for applying a statistical pattern classification algorithm to generate consensus sequences for the IAs, code for catenating consensus sequences with sequences in CCs, and a computer-readable storage medium comprising the codes.

In some embodiments, a system (e.g., a data processing system) that determines at least one consensus sequence from a set of replicate sequences includes a processor, a computer-readable medium operatively coupled to the processor for storing memory, wherein the memory has instructions for execution by the processor, the instructions including one or more of the following: instructions for receiving input of replicate sequence reads, instructions for grouping replicate sequence reads, instructions for analyzing call quality, instructions that align the replicate sequence reads, instructions that determine a percent majority count at positions in the replicate sequence reads, instructions that identify IAs, instructions that apply a statistical pattern classification algorithm to generate at least one consensus sequence (e.g., a "best" consensus sequence, and optionally one or more additional consensus sequences), instructions that catenate consensus sequence from an IA with sequence from adjacent CCs, instructions that compute/store information related to various steps of the method (e.g., quality scores, error rates, etc.), and instructions that record the results of the method.

In certain embodiments, various steps of the method utilize information and/or programs and generate results that are stored on computer-readable media (e.g., hard drive, auxiliary memory, external memory, server; database, portable memory device (CD-R, DVD, ZIP disk, flash memory cards, etc.), and the like. For example, information used for and results generated by the methods that can be stored on computer-readable media include but are not limited to replicate sequence information, majority call percentages, MSAs, DAGs, IAs, CCs, newly generated consensus sequences, newly generated catenated sequences, quality information, technology information, and homologous or reference sequence information.

In some aspects, the invention includes an article of manufacture for determining at least one consensus sequence from replicate sequence reads that includes a machine-readable medium containing one or more programs which when executed implement the steps of the invention as described herein.

Figure 6:
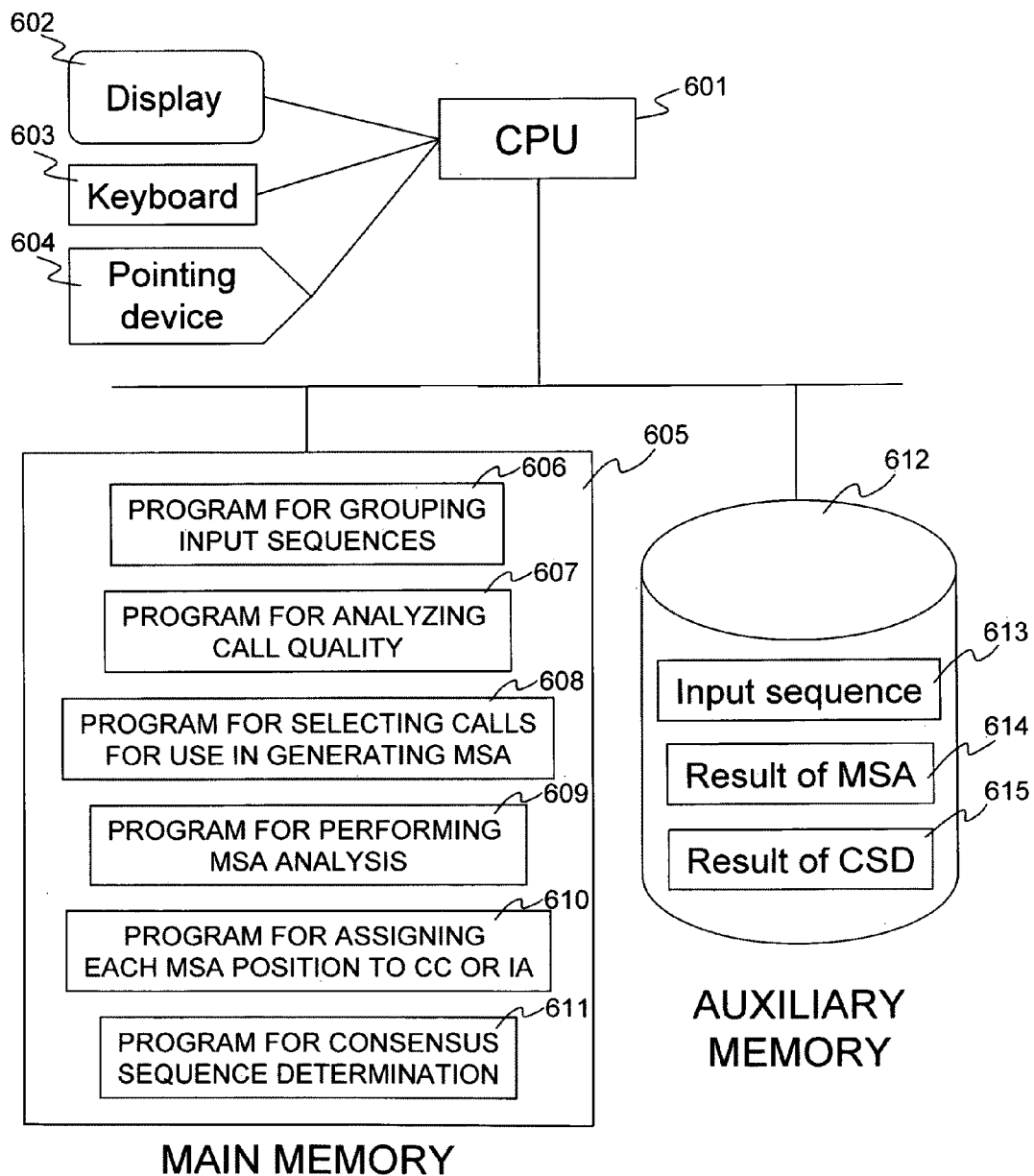
FIG. 6 provides a representative example of a configuration of a device for consensus sequence determination.

FIG. 6 is a block diagram showing a representative example of a configuration of a device for consensus sequence determination in which various aspects of the invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 6 shows an information appliance (or digital device) 600 that may be understood as a logical apparatus that can read information (e.g., instructions and/or data) from auxiliary memory 612, which may reside within the device or may be connected to the device via, e.g., a network port or external drive. Auxiliary memory 612 may reside on any type of memory storage device (e.g., a server or media such as a CD or floppy drive), and may optionally comprise multiple auxiliary memory devices, e.g., for separate storage of input sequences, results of MSA, results of CSD, and/or other information. Device 600 can thereafter use that information to direct server or client logic, as understood in the art, to embody aspects of the invention.

One type of logical apparatus that may embody the invention is a computer system as illustrated in FIG. 6, containing a CPU 601 for performing calculations, a display 602 for displaying an interface, a keyboard 603, and a pointing device 604, and further comprises a main memory 605 storing various programs and a storage device 612 that can store the input sequence 613 and results of multiple sequence alignment (MSA) 614 and consensus sequence determination (CSD) 615. The device is not limited to a personal computer, but can be any information appliance for interacting with a remote data application, and could include such devices as a digitally enabled television, cell phone, personal digital assistant, etc. Information residing in the main memory 605 and the auxiliary memory 612 may be used to program such a system and may represent a disk-type optical or magnetic media, magnetic tape, solid state dynamic or static memory, etc. In specific embodiments, the invention may be embodied in whole or in part as software recorded on this fixed media. The various programs stored on the main memory can include a program 606 to group the input sequences that contain sequence for a given target sequence, a program 607 to analyze the quality of the calls in the input sequence, a program 608 to identify calls to be included in the MSA analysis, a program 609 to carry out the MSA analysis, a program 610 to assign each position in the MSA to a CC or an IA, a program 611 to apply a model to determine consensus sequences for each IA, and a program to catenate IA consensus sequences with CC majority calls to generate a target consensus sequence. The lines connecting CPU 601, main memory 605, and auxiliary memory 612 may represent any type of communication connection.

After input replicate sequences and parameters required for the method of the present invention are specified by the display 602 (also referred to as a "screen"), the keyboard 603, and the pointing device 604, the CPU 601 executes the program stored in the main memory 605 and the MSA and CSD are performed by the methods of the present invention. The input sequence 613 is read from the storage device 612. The output result of MSA 614 and CSD 615 can be stored into the storage devices 612. During the progress of MSA and CSD by the method of the present invention, the progress of this processing can be displayed on the display 602. After completing this processing, the result of the processing can be also displayed on the display 602, saved to an additional storage device (e.g., ZIP disk, CD-R, DVD, floppy disk, flash memory card, etc.), or displayed and/or saved in hard copy (e.g., on paper). The result of the processing may be stored or displayed in whole or in part, as determined by the practitioner. For example, the results for one or more positions, or one or more IAs, or one or more combinations of IAs and CCs may be displayed/saved. These results may further comprise quality information, technology information (e.g., peak characteristics, expected error rates), alternate (e.g., second or third best) consensus sequences, confidence metrics, etc, as described in greater detail above.

VI. Other Considerations

As will be appreciated by those of ordinary skill in the art, various operations described herein may be applied iteratively to increase the performance of the consensus sequence determination methods. For example, the entire process may be iterated with a first iteration using only the data deemed to be of the highest quality, and subsequent iterations further including lower quality data. After each iteration, metrics could be run to provide a quality score for the consensus sequence and/or individual positions within the consensus sequence, and these quality scores would be used to appropriately weight the impact of each position on the consensus sequence determination, e.g., for the next iteration. Such iterative embodiments could allow the highest quality calls to have a greater impact on the final consensus sequence determination than lower quality calls. Another example of iteration of the methods for consensus sequence determination is a method in which a first iteration determines CCs and IAs as described above, and identifies consensus sequences for each IA. In a second iteration the consensus sequences that were determined for each IA in the first iteration are defined as CCs, and the CCs from the first iteration are defined as IAs; consensus sequences are determined for each newly defined IA. This method would be of particular interest in situations where positions in the MSA have a relatively low average percent of majority calls indicating a high degree of miscalls throughout the sample sequences. A related iterative approach is employed the in the construction of HMMs for gene sequences is template expectation maximization. In this approach the template states are changed to find a template and error parameters that best explain a set of training sequences. See, e.g., Durbin, R., et al., *Biological Sequence Analysis: Probabilistic Models of Proteins and Nucleic Acids*, Cambridge University Press, 1998.

In addition, this methodology provides a starting point for estimation of per-base consensus quality values. The quality of the sequence in the IAs is expected to be related to the absolute likelihood of the best sequence, as well as the relative likelihood of this sequence versus all other potential calls (i.e. normalizing by the denominator in the Bayes' formula described above). It might be the case that other formulations for comparing the absolute likelihoods (for example, take the spread of the top three) would provide more robust estimates of the local consensus accuracy.

Other probabilistic or statistical classification approaches that provide the desired likelihood estimate and which might incorporate trace information are also contemplated. For example, a Bayesian network could be trained from observations of real data (basecalls plus trace features) as conditioned on the true template sequence. Other algorithms which could be suggested in this space include kernel methods, nearest-neighbor methods, neural networks, support-vector machines, classification and regression trees (CART), and variations of these.

In the exemplary method described above, the consensus quality estimates for the CCs would be "100%" but a simple Bayes model (for example, see G. A. Churchill, M. S. Waterman (1992) "The Accuracy of DNA Sequences: Estimating Sequence Quality," *Genomics* 14: 89-98) could be introduced which relaxes this restriction and relates the quality estimates for the CCs to the underlying estimates of the quality for each read.

The present methods are also useful for genotyping applications, and the increased accuracy in consensus sequence determination is particularly useful in identifying true heterozygous calls (e.g., using a reference sequence to inform) and detecting rare variants. For example, detection of rare variants is facilitated by the methods herein when replicate sequences are duplicate sequences from a single source. As described above, such duplicate sequences may be generated by various methods, including repeatedly sequencing the same molecule and/or sequencing a template comprising multiple copies of a target sequence. In some embodiments, the consensus sequences generated by the methods and systems of the invention are compared to homologous sequences from other individuals to determine genetic relatedness between the individuals, e.g., for microorganism strain classification, identification of conserved sequences between organisms, forensic applications, paternity testing, etc. The consensus sequences generated by the methods and systems of the invention are also useful for diagnostic, theranostic, and prognostic applications, e.g., to determine an individual's risk of developing genetically-influenced disorder and/or an appropriate treatment regimen for the individual. In some embodiments, the consensus sequences generated by the methods and systems are used to discover and/or assemble genomic sequences for an organism, or to augment genomic sequences previously assembled. Further, it is contemplated that the consensus sequences may be provided (e.g., sold) to third parties, such as the individual from which the original sample was obtained/extracted, research laboratories, clinical laboratories, forensic laboratories, medical professionals, etc. Business methods for relationships with such third parties including the transfer of consensus sequence data in exchange for funding (e.g., equity investment, fee-for-service, etc.) are also contemplated.

Finally, the methods provide increased flexibility, allowing the application of various error models to the process that cannot be used with the traditional position-by-position analysis methods. For example, the concept of analyzing of a plurality of sequential ambiguous calls provides an advantage over known methods for identification of insertions and deletions in sequencing reads. Reads from sequence-by-incorporation methodologies sometimes contain extra or missing base calls, termed "insertions" and "deletions" although the actual template contains no such mutations. Insertions can occur when aberrant incorporation signals are generated when bases that are not incorporated in to the nascent strand are illuminated and detected within the reaction volume; and deletions can occur when an incorporation event occurs without detection of the incorporated base. The base-by-base consensus sequence determination methods commonly used are ineffective at identifying such insertions and deletions in the reads due to their complete dependence on the underlying MSA, which is typically of poor quality when the sequences contain significant numbers and/or lengths of insertions and/ or deletions. In contrast, the methods presented herein are better able to identify such aberrant calls in the reads because the types of error models that can be used with the methods herein can model the system being used to generate the sequences, and can therefore incorporate not only quality values for single calls or positions, but also nonlocal effects such as expected errors based on flanking sequences, detection methods, platform limitations (e.g., reliable readlength), etc. that cannot be accounted for using the traditional position-by-position consensus sequence determination methods.

It is to be understood that the above description is intended to be illustrative and not restrictive. It readily should be apparent to one skilled in the art that various modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. Throughout the disclosure various references, patents, patent applications, and publications are cited. Unless otherwise indicated, each is hereby incorporated by reference in its entirety for all purposes. All publications mentioned herein are cited for the purpose of describing and disclosing reagents, methodologies and concepts that may be used in connection with the present invention. Nothing herein is to be construed as an admission that these references are prior art in relation to the inventions described herein.

VII. Example I

Modeling Errors in a Sequencing-by-Synthesis Experiment with Hidden Markov Models Assessing the performance of a single-molecule, real-time sequencing system relies on comparisons between the sequence of a known template and the sequence emitted by an experiment. A hidden Markov model (HMM) was constructed to analyze the accuracy of sequencing-by-synthesis experiments and provide accurate estimates of system parameters, and this model is described in detail below.

Mapping Between Sequencing Procedures and Hidden Markov Models

Figure 7:
FIG. 7 provides an illustrative example of a directed acyclic graph. The example entitled "Mapping between Sequencing Procedures and Hidden Markov Models" refers to this figure.

The hidden Markov model used employs a very simple underlying state structure that models the progression of the polymerase along its template. At each time step the molecule can move forward to the next template location or stay at the current template location (FIG. 7). The states of the HMM (except the final state) are in one to one correspondence with template locations.

At each transition the model either emitted a symbol that represented one of the four nucleotides of DNA (A, C, G, or T) or did not yield an observation. The symbols ε was used to denote the special case where no observation was emitted, and this case is referred to as the null observation. The Markov model used was one where transitions between discrete states happen at each time step. The additional assumption was made that at time t=0 there had been no observations. In the language of hidden Markov models the individual states were given by:

$$S=\{S_0, S_1, S_2, \ldots, S_N\}$$

and the state of the model at time t was $q_t$. A transition matrix described the probability of arriving at state $S_j$ at time t given that the system is in state $S_i$ at time t−1:

$$a_{ij}=P(q_t=S_j|q_{t-1}=S_i) \text{ where } 0 \leq i \leq j \leq N$$

FIG. 7 provides a graphical representation of the states and transition probabilities of the HMM. Briefly, a standard hidden Markov model yields an observation for each time step.

The distribution of the observations received is a function only of the state of the system at that time. To capture the dynamics of a noisy sequencing-by-synthesis process, the observation distribution was modeled as a function of the observation and the pair of states between which a transition occurred. Instead of an observation distribution for each of the N+1 states in the Markov model, an observation distribution was determined for each of the $(N+1)^2$ possible transitions between states:

$b_{ij}(O) = P(O|q_t=S_j, q_{t-1}=S_i)$ where $0 \leq i,j \leq N$

To complete the HMM specification, the initial state distribution $\pi = \{\pi_i\}$ where $\pi_i = P[q_0 = S_i]$ where $0 \leq i \leq N$ The assumption was made that $\pi_0 = 1$ and $\pi_i = 0$ for $1 \leq i \leq N$. The transition probability matrix $A = \{a_{ij}\}$, the symbol probability matrix $B = \{b_{ij}\}$, and the intial state distribution $\pi = \{\pi_i\}$ were collectively referred to using the triple $\lambda = (A, B, \pi)$ which represented the parameters of the hidden Markov model.

Recursion of the Forward Variable

As described above, the distinct observation symbols were given by $\{\epsilon, A, C, G, T\}$ where $\epsilon$ denoted the null observation. The addition of the null observation changed the structure of the HMM more radically: the state sequence and the observation sequence were no longer synchronous and had to be indexed independently. The standard forward variable (used later for computing the probability of a given observation sequence) is $\alpha_t(i) = P(O_1, O_2, \ldots, O_n, q_t = S_i | \lambda)$ where the index t simultaneously represents the number of states the HMM has visited and the number of observations taken. Given the null observation the forward variable was given by $\alpha_{n,t}(i) = P(O_1, O_2, \ldots, O_n, q_t = S_i | \lambda)$ where $0 \leq n \leq t$ and $0 \leq i \leq N$ Recursive formulae were derived for the forward variable, and at times this required formulae where negative indices occurred. The following definition resulted:

$\alpha_{n,t}(i) = 0$ whenever n<0 or t<0 or i<0

This definition is completely consistent and justifiable with the definition for non-negative indices. The probability of a negative number of observations, a negative time, or negative state number are all equivalently zero. The importance of emphasizing this extension of the definition is apparent below.

The process began by deriving the initial values required by the upcoming recursion formula. Note that $\alpha_{0,0}(0) = P(q_0 = S_0 | \lambda) = 1$ by the previous assumption. It followed that $\alpha_{0,0}(i) = 0$ for $1 \leq i \leq N$. For $t \geq 0$ a recursive formula was developed by summing over all states of the model at a previous time state. Because it was possible not to encounter an observation during a transition:

$\alpha_{n,t+1}(j) = P(O_1, O_2, \ldots O_n, q_{t+1} = S_j | \lambda)$ $= \sum_{i=0}^{N} P(O_1, O_2, \ldots O_{n-1}, q_t = S_i | \lambda) a_{ij} b_{ij}(O_n) +$ $\sum_{i=0}^{N} P(O_1, O_2, \ldots, O_n, q_t = S_i | \lambda) a_{ij} b_{ij}(\varepsilon)$ As a result:

$\alpha_{n,t+1}(j) = \sum_{i=0}^{N} \alpha_{n-1,t}(i) a_{ij} b_{ij}(O_n) + \sum_{i=0}^{N} \alpha_{n,t}(i) a_{ij} b_{ij}(\varepsilon)$ This equation can be simplified due to the sparseness of the transition probability matrix:

$a_{i,i+k} = 0$ whenever k>1

The above recursive formula for $\alpha_{n,t+1}(j)$ then simplifies to $\alpha_{n-1,t}(j-1) a_{j-1,j} b_{j-1,j}(O_n) + \alpha_{n,t}(j-1) a_{j-1,j} b_{j-1,j}(\varepsilon) + \alpha_{n-1,t}(j) a_{jj} b_{jj}(O_n) + \alpha_{n,t}(j) a_{jj} b_{jj}(\varepsilon)$ The above sparse recursion formula only holds for $t \geq 0$, but for the state and observation indices, it applies equally as well with negative values.

Since the forward variable was 0 whenever any of the indices were negative, the following calculations follow from the previous definitions:

$\alpha_{0,1}(0) = \alpha_{0,0}(0) a_{00} b_{00}(\varepsilon) = a_{00} b_{00}(\varepsilon)$ $\alpha_{1,1}(0) = \alpha_{0,0}(0) a_{00} b_{00}(O_1) + \alpha_{1,0}(0) a_{00} b_{00}(\varepsilon) = a_{00} b_{00}(O_1)$ The ordinary practiner will note that these formulae are derived from the sparse recursion formula by removing summands with negative indices. This fact was used freely in upcoming computations.

The Probability of an Observation Sequence Given the HMM

The forward variable was summed over time by defining $A_n(i) = \sum_{t=0}^{T_F} \alpha_{n,t}(i)$ where $T_F$ was the final time. The above rule for negative indices applied equally well to $A_n(i)$. Whenever n or i was negative, the following was true:

$A_n(i) = \sum_{t=0}^{T_F} \alpha_{n,t}(i) = 0$ since by defintion of $\alpha_{n,t}(i)$, all of the summands would be zero. In every case, with the exception of n=0 and i=0 the sparse recursive formula for $\alpha_{n,t}(i)$ could be substituted to solve for $A_n(i)$:

$A_n(i) = \dfrac{A_{n-1}(i) a_{ii} b_{ii}(O_n) + A_{n-1}(i-1) a_{i-1,i} b_{i-1,i}(O_n) + A_n(i-1) a_{i-1,i} b_{i-1,i}(\varepsilon)}{1 - a_{ii} b_{ii}(\varepsilon)}$ Fortunately, the case $A_0(0)$ could be derived from the definition of $\alpha_{0,t}(0)$, previously derived:

$A_0(0) = \sum_{t=0}^{\infty} \alpha_{0,t}(0) = \sum_{t=0}^{\infty} (a_{00} b_{00}(\varepsilon))^t = \dfrac{1}{1 - a_{00} b_{00}(\varepsilon)}$ By using the rule for negative indices the recursion can be initiated. The first few recursions are as follows:

$$A_1(0) = \frac{A_0(0)a_{00}b_{00}(O_1)}{1-a_{00}b_{00}(\varepsilon)} = \frac{a_{00}b_{00}(O_1)}{(1-a_{00}b_{00}(\varepsilon))^2}$$

$$A_0(1) = \frac{A_0(0)a_{01}b_{01}(\varepsilon)}{(1-a_{11}b_{11}(\varepsilon))} = \frac{a_{01}b_{01}(\varepsilon)}{(1-a_{00}b_{00}(\varepsilon))(1-a_{11}b_{11}(\varepsilon))}$$

The probability of an observation sequence $O_1, O_2, \ldots, O_L$ was given by $A_L(N)$ where L is the length of the observation sequence and as previously defined, N is the last state of the HMM.

Transition and Observation Matrices Derived from Templates

Each state of the HMM models a location along the template DNA strand where the synthesizing polymerase resided between incorporation events. There are two classes of transitions that occurred from this state:

1. The polymerase incorporated a base and proceeded one position along the template.
2. The polymerase bound a nucleotide, but unbound before the incorporation event (a "branch") or a labeled nucleotide "stuck" transiently to the surface of the ZMW, inside the illumination region. In this case the polymerase did not move along the template.

Since the first process moved the state along the state chain by one position, this was referred to as the "move" transition, and its probability was denoted by $a_{i,i+1}$. The second process left the state in the same position so this was referred to as the "stay" transition with probability given by $a_{i,i}$.

A correct incorporation emitted the symbol corresponding to the current template location. A branch emitted the symbol corresponding to the current template location while a stick generated a random symbol. The probability of branching and sticking was modeled as a function of the observation symbol (including the null observation symbol). The probability (per time step) of branching and sticking was denoted as follows:

$P(\text{branch}|X)=b(X), P(\text{stick}|X)=s(X)$ where $X\in\{\varepsilon,A,C,G,T\}=\Theta$ Emissions from the sequencing-by-incorporation system can be obscured by noise in the signal collection system and can result in missed emissions or emissions that are classified as the wrong symbol (e.g., basecall). As such, the probability that an emisson is missed or misclassified was also modeled as dependent on the symbol, and these probabilities were labeled $P(\text{missed}|X)=d(X), P(\text{misclassified}|X)=m(X)$ where $X\in\Theta$ Here d stood for "dark" and m for "misclassified." In this way a set vectors was defined $\mu=\{b,s,d,m\}$. For example, the components of vector b were the probabilities of branching for a given observation symbol. $\mu$ was referred to as the set of error parameters of the hidden Markov model.

Transition and observation matrices were created based on a known DNA template. Since the states of the model (except the terminal state) were in one to one correspondence with the bases in the DNA template, the transition probabilities at a given state were dependent on which base was in the DNA template at the corresponding position.

A "stay" transition occurred only as the result of a branch or stick. The probability of branching was dependent on the current base. The problem was that the probability of sticking was independent of the current base. A means of "summing" these incongruous probabilities was needed. An invertible transform was used to convert these probabilities to expected values, sum the expected values, and then recover the normalized probability via the inverse transform. If the discrete random variable was the count of branches in the event of having n successive branches and then 1 non-branch, it followed that the corresponding probability distribution on the set $\{0, 1, 2, 3, \ldots\}$ was a discrete exponential distribution of the form $P(n)=b(X)^n(1-b(X)), X\in\Theta$ The expected value of the random variable is $$\sum_{n=0}^{\infty} nb(X)^n(1-b(X)) = (1-b(X))\sum_{n=0}^{\infty} nb(X)^n$$
$$= (1-b(X))\frac{b(X)}{(1-b(X))^2}$$
$$= \frac{b(X)}{1-b(X)}$$

By a similar construction, the expected value of the corresponding random variable for sticking was $$\sum_{X\in\Theta} \frac{s(X)}{1-s(X)}$$

noting that each nucleotide specific sticking probability was transformed independently since the expectation operator was linear. Assuming that the first template of the nucleotide is "A," the expected value of "staying" was computed by summing the above two results:

$$e = \frac{b(A)}{1-b(A)} + \sum_{X\in\Theta} \frac{s(X)}{1-s(X)}$$

The probability of staying was then $$a_{00} = \frac{e}{1+e}$$

by applying the inverse transform. The net result was a normalized sum of probabilities. The "move" transition probability was then $a_{01}=1-a_{00}$. This process was repeated at each position in the template to generate all nonzero transition probabilities.

The symbol observation matrix was generated as follows. At each position in the template a vector of probabilities was defined with one probability for each of the symbols $X\in\Theta$. If the first nucleotide in the template is "A," the following was true $$P(\text{branch}|\text{stay, base}=A) = \begin{cases} 0 & \text{if } P(\text{stay})=0 \\ \dfrac{\frac{b(A)}{1-b(A)}}{\frac{b(A)}{1-b(A)} + \sum_{X\in\Theta}\frac{s(X)}{1-s(X)}} & \text{otherwise} \end{cases}$$

This formula was justified as follows: Let $X=\{x_1, x_2, \ldots, x_n\}$ be a large sample of a binomial random variable where $$X = \begin{cases} 1 & \text{if the event is a branch} \\ 0 & \text{if the event is not a branch} \end{cases}$$

Similarly, a large sample of a binomial random variable was denoted as $S=\{s_1, s_2, \ldots, s_n\}$ where $$S = \begin{cases} 1 & \text{if the event is a stick} \\ 0 & \text{if the event is not a stick} \end{cases}$$

The above ratios of expected values resulted in the appropriate probabilities. Since the mean approximated the expected value for large n, $$\frac{\frac{1}{n}\sum_{i=1}^{n}x_i}{\frac{1}{n}\sum_{i=1}^{n}x_i + \frac{1}{n}\sum_{i=1}^{n}s_i} = \frac{\sum_{i=1}^{n}x_i}{\sum_{i=1}^{n}x_i + \sum_{i=1}^{n}s_i}$$

$$= \frac{\text{number of branches}}{\text{number of stays}}$$

$$= P(\text{branch} \mid \text{stay})$$

Similarly, $$P(\text{stick} \mid \text{stay}, \text{base} = A) = \begin{cases} 1 & \text{if } P(\text{stay}) = 0 \\ \dfrac{\sum_{X \in \Theta} \dfrac{s(X)}{1-s(X)}}{\dfrac{b(A)}{1-b(A)} + \sum_{X \in \Theta} \dfrac{s(X)}{1-s(X)}} & \text{otherwise} \end{cases}$$

For each symbol $Y \in \{A,C,G,T\} = \Omega$, a preliminary value was constructed that combines the two probabilities just described. P(branch|stay, base=A) was added to a "weighted" P(stick|stay, base=A), where the weighting was the proportion of sticking due to the given symbol $Y \in \Omega$:

$P(\text{branch or stick}, Y \mid \text{stay}, \text{base} = A) =$ $$\begin{cases} \dfrac{\dfrac{s(Y)}{1-s(Y)}}{\sum_{X \in \Theta} \dfrac{s(X)}{1-s(X)}} & \text{if } P(\text{stay}) = 0 \\[2ex] \dfrac{\dfrac{b(A)}{1-b(A)} + \dfrac{s(A)}{1-s(A)}}{\dfrac{b(A)}{1-b(A)} + \sum_{X \in \Theta} \dfrac{s(X)}{1-s(X)}} & \text{if } P(\text{stay}) \neq 0, Y = A \\[2ex] \dfrac{\dfrac{s(Y)}{1-s(Y)}}{\dfrac{b(A)}{1-b(A)} + \sum_{X \in \Theta} \dfrac{s(X)}{1-s(X)}} & \text{if } P(\text{stay}) \neq 0, Y \neq A \end{cases}$$

A vector $v_{b,s}$ of length 5 was constructed that took 0 as the first component and appended P(branch or stick, Y|stay, base=A) for each $Y \in \Omega$ ordered via $\{A, C, G, T\}$. Given the error parameters $\mu = \{b,s,d,m\}$, the next goal was to apply some column-wise stochastic matrices to this vector $v_{b,s}$ to account for the dark and misclassified errors in the system. First, a dark matrix was constructed that contains estimates of the probability that a given symbol would be missing. The probabilities from the error parameter vector d were distributed columnwise between the null symbol $\epsilon$ and one of the actual nucleotide symbols. For example, if it was assumed that each actual nucleotide symbol would be obscured by the noise in the system 25% of the time, the column-wise stochastic dark matrix had the form $$D = \begin{pmatrix} 1 & .25 & .25 & .25 & .25 \\ 0 & .75 & 0 & 0 & 0 \\ 0 & 0 & .75 & 0 & 0 \\ 0 & 0 & 0 & .75 & 0 \\ 0 & 0 & 0 & 0 & .75 \end{pmatrix}$$

Similarly a column-wise stochastic mixing matrix M was constructed to incorporate the prior knowledge of misclassification on a per-symbol basis. Now a vector could be computed containing the observation probabilities for the "stay" transition $$b_{00} = M \cdot D \cdot v_{b,s}$$

$v_Y$ was allowed to be constructed by having 0 in the first component and 1 in the component associated to $Y \in \Omega$, and a vector was computed containing the observation probabilities for the "move" transition $$b_{01} = M \cdot D \cdot v_i$$

This process was repeated at each position in the template to generate all nonzero observation probabilities. In other words, an observation vector v was multiplied by the miscall matrix and the dark matrix to get the final observation matrix.

Recursion of the Backward Variable

For a standard HMM where the observations and states are in one-to-one correspondence, the backward variable (used later for error parameter estimation) is given as $$\beta_t(i) = P(O_{t+1}, O_{t+2}, \ldots, O_{T_F} \mid q_t = S_i, \lambda)$$

where $T_F$ is the final time. In the instant example, because observations and states are not synchronous, the following definition was employed $$\beta_{n,t}(i) = P(O_{n+1}, O_{n+2}, \ldots, O_L \mid q_t = S_i, \lambda)$$

where $O_L$, was the last observation. This was the probability of observing the partial observation sequence $O_{n+1}$, $O_{n+2}, \ldots, O_L$ after arriving at state $S_i$ at time t. As in the case of the forward variable, a recursion formula was needed, as well as some initial values to begin the recursion. The assumption was made that arrival at the final state $S_n$ only occurred at the terminal time $T_F$. Some initial values $\beta_{L,t}(N)$ for $0 \leq t \leq T_F$ were determined. Note that $$\beta_{L,t}(N) = P(\text{No Observations} \mid q_t = S_N, \lambda)$$

Given the assumption above, the following was true $$\beta_{L,t}(N) = 0 \text{ for } 0 \leq t < T_F \text{ and } \beta_{L,T_F}(N) = 1$$

The last equality followed since there were no transitions after the final state and therefore no observations since the model had observations only at transitions.

In a similar manner (and consequence) to the forward variable, it was logically consistent to define $$\beta_{n,t}(i) = 0 \text{ whenever } n > L \text{ or } t > T_F \text{ or } i > N$$

The probability of having more than L observations (given the observation sequence of length L), times past the final time, or states past the final state was equivalently 0.

For $t<T_F$, a recursive formula was developed for the backward variable. In a manner symmetric to the forward variable, the recursion was accomplished by summing a succeeding time step across all states of the model. From the previous definition $$\beta_{n,t}(i)=P(O_{n+1},O_{n+2},\ldots,O_M|q_t=S_i,\lambda)$$

it followed that $$\beta_{n,t}(j) = \sum_{i=0}^{N} P(O_{n+2},\ldots,O_M | q_{t+1} = S_i, \lambda) a_{ji} b_{ji}(O_{n+1}) +$$

$$\sum_{i=0}^{N} P(O_{n+1},\ldots,O_L | q_{t+1} = S_i, \lambda) a_{ji} b_{ji}(\varepsilon)$$

As usual, the sparseness of the transition probability matrix was used to conclude $$\beta_{n,t}(j)=a_{jj}b_{jj}(O_{n+1})\beta_{n+1,t+1}(j)+a_{j,j+1}b_{j,j+1}(O_{n+1})\beta_{n+1,t+1}(j+1)+a_{jj}b_{jj}(\varepsilon)\beta_{n,t+1}(j)+a_{j,j+1}b_{j,j+1}(\varepsilon)\beta_{n,t+1}(j+1)$$

This formula holds only for $t<T_F$, but when $n>L$ or $j>N$ the associated backward variable may be replaced with 0.

As in the case of the forward variable, the following was defined:

$$B_n(i) = \sum_{t=0}^{T_F} \beta_{n,t}(i)$$

When $n>L$ or $i>N$, $B_n(i)=0$ from the definition of $\beta_{n,t}(i)$.

Except in the case $n=L$ and $i=N$, the summands in the definition of $B_n(i)$ could be replaced by the sparse recursive formula and solved for $B_n(i)$:

$$B_n(i) = \frac{a_{ii}b_{ii}(O_{n+1})B_{n+1}(i) + a_{i,i+1}b_{i,i+1}(O_{n+1})B_{n+1}(i+1) + a_{i,i+1}b_{i,i+1}(\varepsilon)B_n(i+1)}{1 - a_{ii}b_{ii}(\varepsilon)}$$

The value of $B_L(N)$ could be solved using the definition of $\beta_{n,t}(i)$ above:

$$B_L(N) = \sum_{t=0}^{T_F} \beta_{L,t}(N) = 1$$

Again, the recursion could be initiated by using the rule for negative indices. The first few recursions were as follows:

$$B_L(N-1) = \frac{a_{N-1,N}b_{N-1,N}(\varepsilon)B_L(N)}{1 - a_{N-1,N-1}b_{N-1,N-1}(\varepsilon)}$$

$$= \frac{a_{N-1}b_{N-1,N}(\varepsilon)}{1 - a_{N-1,N-1}b_{N-1,N-1}(\varepsilon)}$$

$$B_{L-1}(N) = 0$$

Uses of the Hidden Markov Model

The above description provides a method for taking a source template T and a set of error parameters $\mu=(b,s,m,d)$ and calculating the transition and observation probabilities over a possible read R. Using the notations described above, the following equation was derived $$P(R|T,\mu)=P(O_1,O_2,\ldots,O_L)=A_L(N)$$

where R was the set of observations constituting the read, L was the number of observations in the read, and N was final state of the of the HMM, or the number of bases in the template. The HMM then had N+1 states as previously defined.

This equation was used in two ways: parameter estimation and consensus generation. Parameter estimation is the problem of learning the error parameters $\mu$ given a set of reads from known templates:

$$\{(R_i,T_i)|1\leq i\leq K\}$$

Without any prior information about $\mu$ a simple maximum likelihood estimator was constructed $$\mu_{ML} = \underset{\mu}{\mathrm{argmax}}\prod_{i=1}^{K} P(R_i | T_i, \mu)$$

Another problem to which the HMM was applicable was that of determining the true template that generated a series of error-prone reads: to generate the best consensus sequence T given a set of reads $\{R_i\}$ from that template and the error parameters $\mu$. Again, assuming no prior knowledge of the template, the maximum likelihood estimate was constructed $$T_{ML} = \underset{T}{\mathrm{argmax}}\prod_{i=1}^{K} P(R_i | T, \mu)$$

The manner is which the parameter optimization problem was addressed is presented below.

Error Parameter Estimation

As mentioned above, one goal was solving the problem of learning the error parameters $\mu=(b,s,m,d)$ given a set of reads from known templates:

$$\{(R_i,T_i)|1\leq i\leq K\}$$

A method was needed to efficiently search the space of error parameters $\mu=(b,s,m,d)$ to find $$\mu_{ML} = \underset{\mu}{\mathrm{argmax}}\prod_{i=1}^{K} P(R_i | T_i, \mu)$$

One apparent solution to this problem would be to construct a hidden Markov model with parameters $\lambda=(A, B, \pi)$ (as described above in "*Transition and Observation Matrices Derived from Templates*") for every set of error parameters $\mu$ and every template $T_i$, and for each read $R_i$ compute $P(R_i|T_i,\mu)$ (as described above in "*The Probability of an Observation Sequence Given the HMM*"). The computational complexity of such an approach was not feasible.

The method actually used started with the hidden Markov model constructed from a template T using an initial guess at the error parameters $\mu=(b,s,m,d)$. For a given read R, a vector of statistics that were summarized per base and normalized to allow for template-free comparisons were computed using the method described below. For a given set of error parameters µ=(b,s,m,d), the methods described above (in "*Transition and Observation Matrices Derived from Templates*") were used to derive a vector of statistics identical in form to the summary statistics just described. A gradient method (in this case the Levenberg-Marquardt algorithm) was subsequently used to search the space of error parameters µ=(b,s,m,d) to find the error parameters that minimize the "difference" between the summary statistics of the error parameter, and the summary statistics of the read and model.

For a model with parameters λ=(A, B, π) that had been generated from a template T as described above (in "*Transition and Observation Matrices Derived from Templates*"), and a read R, with observation sequence $O_1, O_2, \ldots, O_L$, n was defined as a position between 1 and L. First, is was claimed that $$A_n(i) = \sum_{t=0}^{T_F} \alpha_{n,t}(i)$$

was the expected number of times when generating a random output sequence from the model, that $O_1, O_2, \ldots, O_n$ was generated and that the model is in state $S_i$. Similarly $$B_n(j) = \sum_{t=0}^{T_F} \beta_{n,t}(j)$$

was the expected number of times when generating a random output sequence from the model, that was generated after starting from state $S_j$. The forward case was proved as follows, noting that the proof for the backward case was identical.

First, the following discrete random variable was defined $$X = \begin{cases} 1 & \text{if at time } t \text{ we have observed } O_1, O_2, \ldots, O_n \text{ and } q_i = S_i \\ 0 & \text{if at time } t \text{ the condition is otherwise} \end{cases}$$

In other words, the random variable X counted the number of times $O_1, O_2, \ldots, O_n$ was observed, and the model was in state $S_i$ at time t. Then, by definition of the expected value of a discrete random variable $$E(X) = 0 \cdot (1 - \alpha_{n,t}(i)) + 1 \cdot \alpha_{n,t}(i) = \alpha_{n,t}(i)$$

To compute the expected count of having observed $O_1, O_2, \ldots, O_n$ and that the model is in state $S_i$ at any time, it follows that $$A_n(i) = \sum_{t=0}^{T_F} \alpha_{n,t}(i)$$

Given these interpretations of the sums of the forward and backward variables over time, it was claimed that $$\xi_{ij}(\varepsilon) = \sum_{n=0}^{L} A_n(i) a_{ij} b_{ij}(\varepsilon) B_n(j)$$

was the expected number of times the null observation occurred when transitioning from $S_i$ to $S_j$. This was proven as follows.

Given the combined event of having observed $O_1, O_2, \ldots, O_n$ with the model in state $S_i$ and having observed $O_{n+1}, O_{n+2}, \ldots, O_L$, after starting from state $S_j$, for a given n this combined event was in one-to-one correspondence with the event of having observed a null observation on the transition from state $S_i$ to $S_j$ under the identical assumption that $O_1, O_2, \ldots, O_n$ was observed with the model in state $S_i$, and $O_{n+1}, O_{n+2}, \ldots, O_L$ was observed after starting from state $S_j$. Note that $$A_n(i) B_n(j)$$

was the number of times this combined event occurred and therefore the number of times the null observation was emitted under these conditions. The probability the null observation occurred when transitioning from state $S_i$ to $S_j$ was $$a_{ij} b_{ij}(\varepsilon)$$

Consider the random variable X, which counts the number of nulls emitted when transitioning from state $S_i$ to $S_j$, given the identical assumptions about the progression of the observation sequence for a given n. By definition of the expected value of a discrete random variable, it followed that $$E(X) = \sum_{n=0}^{L} A_n(i) B_n(j) a_{ij} b_{ij}(\varepsilon) = \xi_{ij}(\varepsilon)$$

and the claim was proved. Another possibility was that there was an observation between state $S_i$ and $S_j$. By an identical argument one could prove the expected number of transitions from state $S_i$ to $S_j$ where a symbol $Y \in \{A,C,G,T\} = \Omega$ is given by $$\xi_{ij}(Y) = \sum_{n=0}^{L-1} A_n(i) B_{n+1}(j) a_{ij} (b_{ij}(Y))$$

is observed.

Finally, it was concluded that the expected number of transitions from state $S_i$ to $S_j$ was given by $$\xi_{ij} = \xi_{ij}(\varepsilon) + \sum_{Y \in \Omega} \varepsilon_{ij}(Y)$$

Note that it could not be summed over the original set of symbols $\Theta = \{\varepsilon, A, C, G, T\}$ because the formula was different for the null observation.

The objective in error parameter estimation was to determine $$\mu_{ML} = \arg\max_{\mu} \prod_{i=1}^{K} P(R_i | T_i, \mu)$$

To achieve this objective, $\xi_{ij}$ and its summands was transformed into statistics that were comparable across reads, templates, and different choices for error parameters. The standard approach at this point is to reestimate the model parameters λ. (See, e.g., L. R. Rabiner (1989) "A Tutorial on Hidden Markov Models and Selected Applications in Speech Recognition," *Proc. IEEE* 77(2):257-286.) These parameters are not only dependent on a template, but there is no tractable way of recovering the error parameters μ from the model parameters λ.

To resolve this problem, $\xi_{i,i}$ and $\xi_{i,i+1}$ were summarized per nucleotide base Y∈Ω:

$$\xi_{stay}(Y) = \sum_{S_i=Y} \xi_{i,i}$$

$$\xi_{move}(Y) = \sum_{S_i=Y} \xi_{i,i+1}$$

where $S_i$=Y meant that the template had nucleotide Y at the ith position. Next $\xi_{i,i}$ and $\xi_{i,i+1}$ was summarized per nucleotide base Y∈Ω and per observation symbol Z∈Θ:

$$\xi_{stay\_obs}(Y, Z) = \sum_{S_i=Y} \xi_{i,i}(Z)$$

$$\xi_{move\_obs}(Y, Z) = \sum_{S_i=Y} \xi_{i,i+1}(Z).$$

The collection ($\xi_{stay}$, $\xi_{move}$, $\xi_{stay\_obs}$, $\xi_{move\_obs}$) was referred to as the sufficient statistics of the read R and the hidden Markov model generated from template T, or more compactly, the sufficient statistics of (R,T).

The sufficient statistics of (R,T) were converted into parameters that were similar to the model parameters, with the exception that they were per base and not dependent on a specific template as in the case λ=(A,B,π). The stay transition probability was first computed per base Y∈Ω:

$$a_{stay}(Y) = \frac{\xi_{stay}(Y)}{\xi_{stay}(Y) + \xi_{move}(Y)}$$

These statistics were carefully normalized, so that the length of the template T would not influence the value. The following "conservative" binomial error formula was used in this normalization:

$$\Psi(p, n) = \frac{\max(p, 1/n) * \max(1 - p, 1/n)}{n}$$

and the following was defined:

$$w_{a_{stay}}(Y) = \Psi(a_{stay}(Y), \xi_{stay}(Y) + \xi_{move}(Y))$$

Since the corresponding transition move probabilities were complementary to the stay probabilities (that is $a_{move}$=1−$a_{stay}$), it was not necessary to include these in the summary statistics.

The stay observation probabilities were computed per base Y∈Ω and observation Z∈Θ:

$$b_{stay}(Y, Z) = \frac{\xi_{stay\_obs}(Y, Z)}{\xi_{stay}(Y)}$$

and the following was defined:

$$w_{b_{stay}} = \Psi(b_{stay}(Y,Z), \xi_{stay}(Y))$$

In a similar manner, the move observation probabilities were computed per base Y∈Ω and observation Z∈Θ:

$$b_{move}(Y, Z) = \frac{\xi_{move\_obs}(Y, Z)}{\xi_{move}(Y)}$$

and the following was defined:

$$w_{b_{move}} = \Psi(b_{move}(Y,Z), \xi_{move}(Y))$$

The required per base and normalized summary statistics were computed, given a read R and hidden Markov model generated from a template T based on some initial guess of the error parameters μ=(b,s,m,d). This was given by $$\{a_{stay}(Y), b_{stay}(Y,Z), b_{stay}(Y,Z) | Y \in \Omega, Z \in \Theta\}$$

The "weights" computed above were used in the minimization function used in the gradient search algorithm. The next task was, given an arbitrary set of error parameters μ=(b,s,m,d), to derive a comparable set of summary statistics that we would compare against the normalized summary statistics derived from (R,T). The derivation laid out above (in "*Transition and Observation Matrices Derived from Templates*") accomplished this task. The identical computations were performed for each nucleotide base and each observation symbol, irrespective of any template, noting that a set of summary statistics identical to those derived from (R,T) could be produced, with the exception that these statistics were template-free.

This last incongruity was accounted for in the way the difference between the summary statistics of (R,T) and the summary statistics of μ=(b,s,m,d) in the minimization function utilized by our gradient search method (the Levenberg-Marquardt algorithm) were measured. For example, if $a_{stay_{(R,T)}}$ and $a_{stay_\mu}$ are corresponding statistics from the set of summary statistics of (R,T) and the summary statistics of μ=(b,s,m,d) respectively, the following equation was used to measure the difference between these statistics:

$$\frac{a_{stay_{(R,T)}}(Y) - a_{stay_\mu}(Y)}{w_{a_{stay}}(Y)}$$

All differences between the statistics were thus transformed with the corresponding weight defined above. The gradient search method then operated on the space of error parameters μ=(b,s,m,d) using the above formula to minimize the difference between the sufficient statistics of (R,T) and the summary statistics of μ=(b,s,m,d). The algorithm monotonically converged to a local maximum.

Error Rate Comparison

Figure 8:
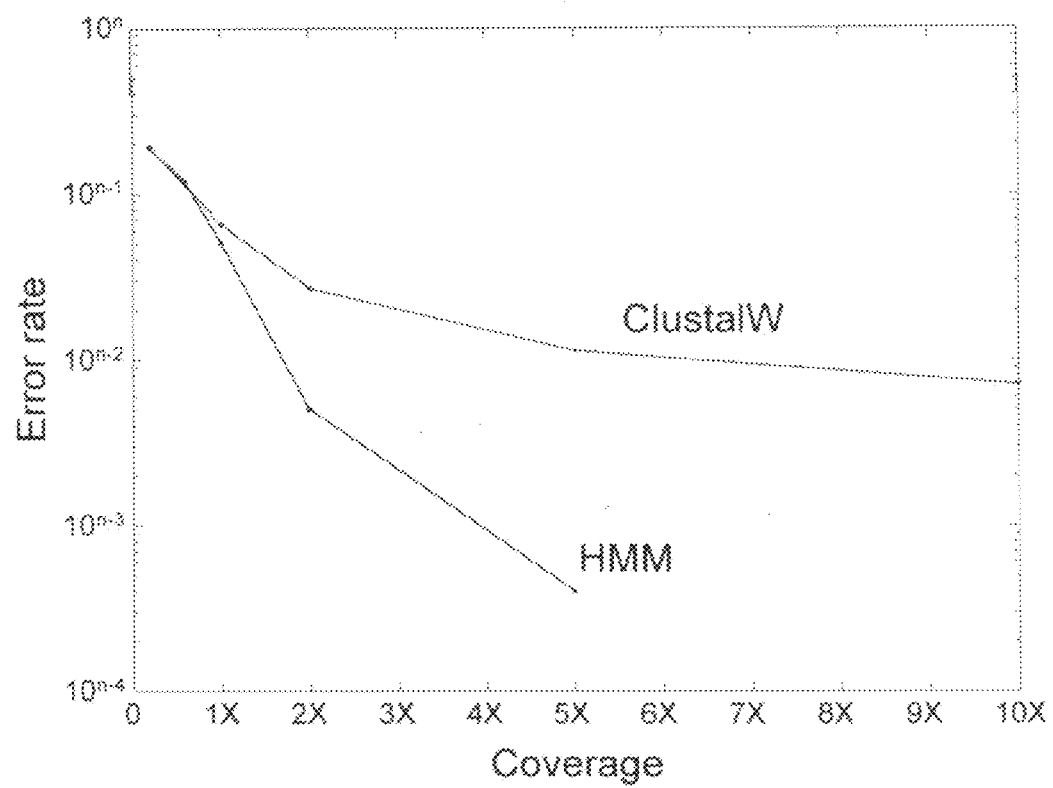
FIG. 8 provides a graphical representation of results from an experiment comparing two methods of consensus sequence determination.

FIG. 8 shows the results from an experiment comparing error rates for the ClustalW method with error rates using methods described herein where HMM is used to determine a consensus sequence across an IA. (ClustalW software and instructions for use are readily available, e.g., from the Conway Institute UCD Dublin.) A random template and a set of HMM error parameters were chosen. A set of simulated reads were generated from the template using the HMM initialized with the chosen error parameters. The consensus sequence was computed using a subset of the simulated reads in two ways: with the HMM as outlined above (e.g., in paragraph [0093]), and with a MATLAB implementation of ClustalW (with parameters tuned to maximize consensus accuracy). The plot in FIG. 8 shows the average consensus accuracy over many trials vs. the number of reads that went into the consensus. Although the HMM methodology has a slightly lower error rate at 1× coverage, it was significantly lower than the ClustalW methodology at 2× coverage, and was over 10-fold lower at 5× coverage. Even at 10× coverage the ClustalW error rate far exceeded that exhibited at 5× coverage using the HMM methodology. These results demonstrated that the methods described herein using HMM to generate consensus sequences could significantly outperform standard MSA methods for determining consensus sequences from replicate sequence reads.

Confidence Metrics

Confidence metrics were developed to provide a measure of the reliability of the consensus sequence generated by the methods herein. The confidence metrics described as follows are meant to be used as a relative measure when assessing the confidence of one call over another, and not to compute exact percentages of confidence intervals, although the latter is also contemplated. Methods for computing confidence intervals are well known and commonly used by those of skill in the art.

Methods for computing confidence values were developed by comparing consensus sequences generated by the methods herein with the known sequence for the template molecule. For IAs, the confidence values were computed by using the log average of the HMM probability (for observing entire set of reads) to impute the central tendency for observing a single read in that set given the template. For CCs, the confidence values were computed by using the plurality percentage along with a penalty function to account for differences/biases due to coverage. The confidence values generated by these methods range from 1-10, with 1 being the least accurate and 10 being the most accurate. These values scale with the accuracy of the call when comparing consensus vs. reference. The raw values are computed as follows:

For IAs: [P(observing read 1|template)*P(observing read 2|template)* . . . * P(observing read n|template)]^(1/n), where n=number of reads For CCs: Fraction(most popular base)−1/e^(coverage)

The raw values are binned to fixed brackets to produce confidence values ranging from 1 to 10.

VIII. Example II

A consensus basecall was determined in an MSA using a pattern classification model that accounted for the local context of the sequence alignment and comprised two steps: (1) estimation of the context-dependent alignment model parameter using whole genome multiple sequence alignment; and (2) use of the estimated model parameters to both determine consensus basecalls and provide a value indicating the discrimination power for the position so basecalled.

For a position in the *E. coli* K12 genome (position 1904826 of the K12 NCBI reference sequence), it was observed that $(n_{j,A}, n_{j,C}, n_{j,G}, n_{j,T}, n_{j,-}) = (2, 5, 10, 8, 7)$ for the "T" base in the "CGTGG" 5-mer. Using the following context-dependent base frequencies from the whole genome multiple sequence alignment of a 47-fold coverage of sequencing reads:

$f_{CGAGG} = (A:0.688953, C:0.0921108, G:0.103457, T:0.0351911, -:0.0802874)$ $f_{CGCGG} = (A:0.0331184, C:0.785788, G:0.0947676, T:0.0317243, -:0.0546016)$ $f_{CGGGG} = (A:0.0384701, C:0.0873947, G:0.809279, T:0.0357317, -:0.0291242)$ $f_{CGTGG} = (A:0.0384287, C:0.0976506, G:0.104326, T:0.681964, -:0.0776305)$, it was found that $E_{T,A}=7.80$, $E_{T,C}=7.70$ and $E_{T,G}=4.5$. With this result, it was concluded that "T" was the most likely base for that particular position according this model. The discrimination power computed as the log-odds ratio between the top two calls, T and G, was determined to be only 4.5 due to the numerous observations of "G" in that position. This discrimination power value was indicative of the confidence that the "T" was indeed the dominant consensus base according to the model. Interestingly, even though $n_G > n_T$ in this example, the model still called "T" as the consensus base. Since the middle base of the 5-mer context is surrounded by other "G" bases, the model took into account both the possibility that the "G's" observed are due to incorrect alignments and the low likelihood of observing a "T" at that position if the correct basecall is indeed a "G." According to the model, the eight "T's" out of 32 observations at that position actually suggested that the base at that position should be "T" rather than "G."

Figure 9:
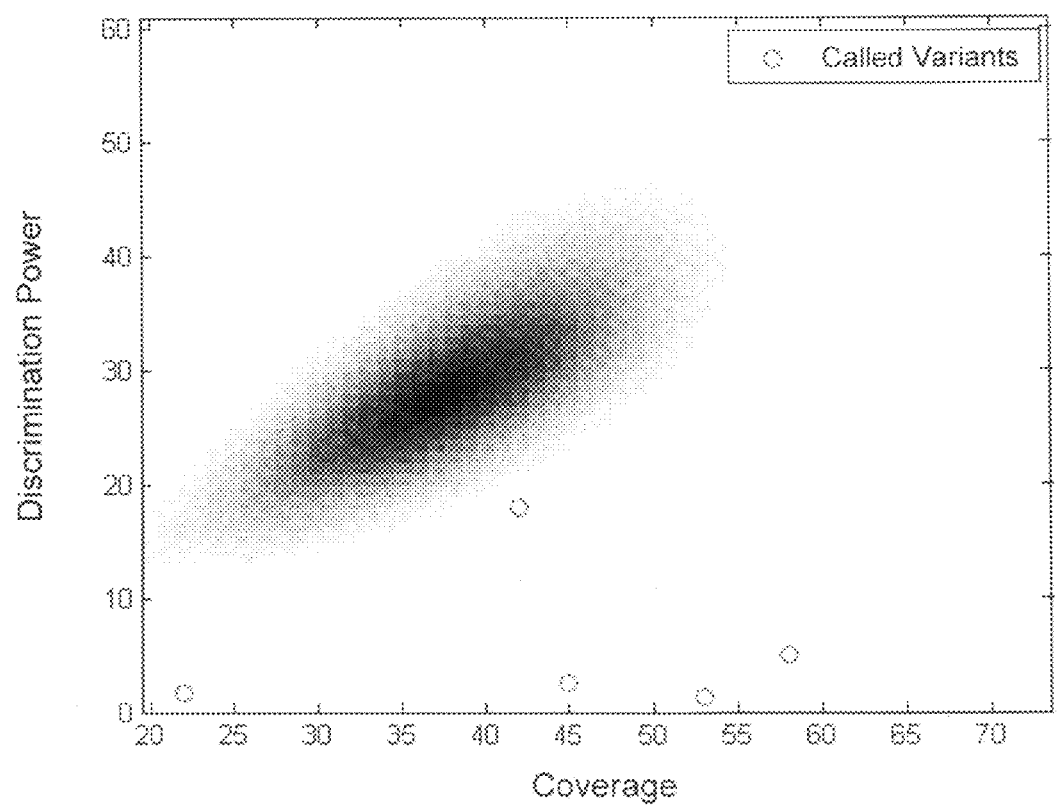
FIG. 9 provides a plot illustrating the distribution of the "discrimination power" against the coverage of a data set described in Example II.

The plot shown in FIG. 9 shows the distribution of the "discrimination power" against the coverage of this data set. The majority of positions of the consensus call had the discrimination power of about 30 and fall within the grey "blob" in the plot. This discrimination power was used for screening out false positives for SNP calling on a data set comprising the K12 genome. For example, the four small circles nearest the x-axis represent calls that were confirmed to be false positives for variant loci by Sanger sequencing. All of these calls had discrimination power of less than about seven. In contrast, the call with a discrimination power of about 18 was confirmed as a true variant by Sanger sequencing.

IX. Example III

Figure 12:
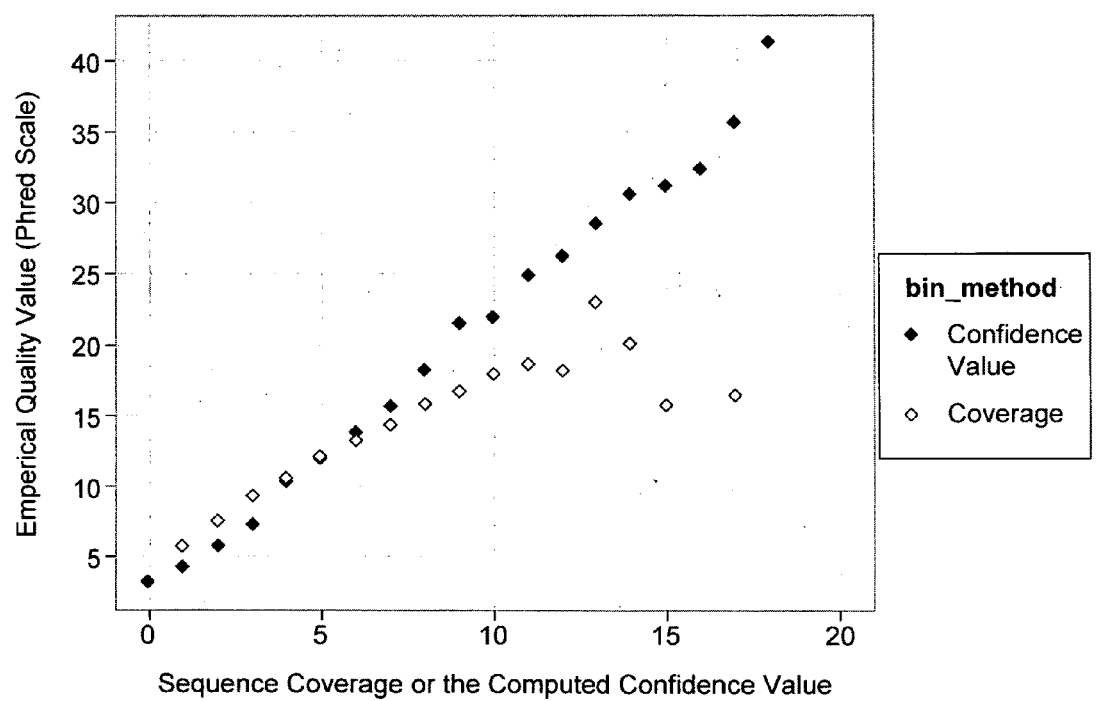
FIG. 12 provides a graphical representation of summed confidence values correlated with empirical Phred-style empirical quality values (EQV) as described in Example III.
Figure 13:
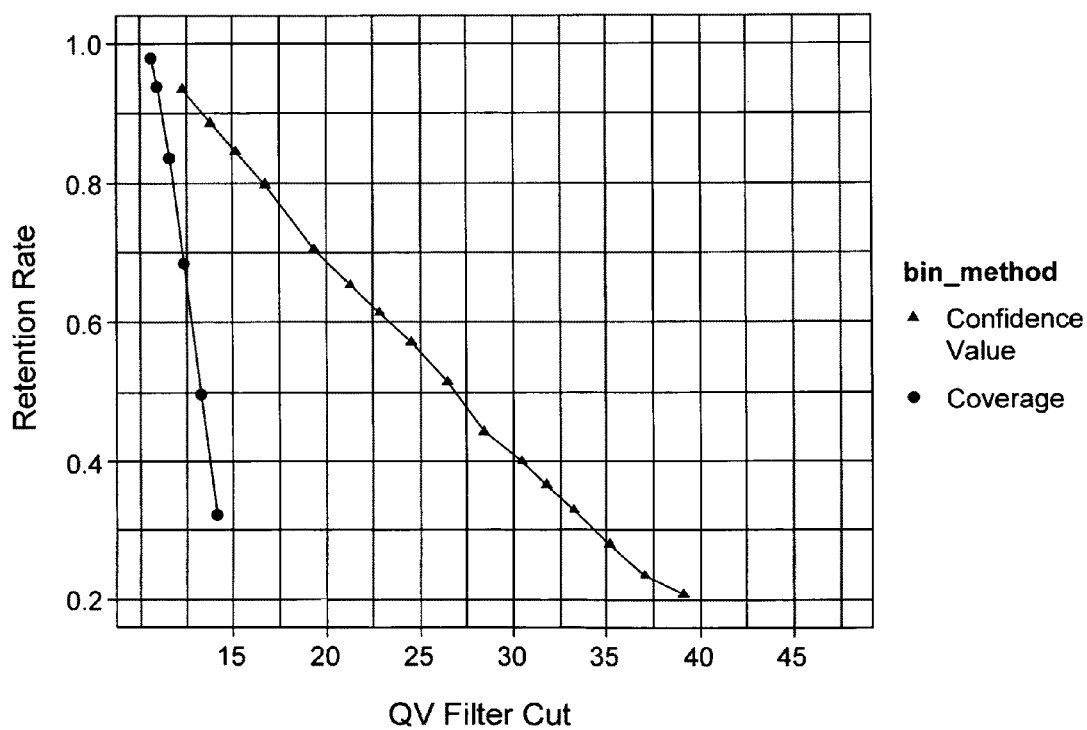
FIG. 13 provides a graphical representation of how many basecalls remained when the consensus bases below a given QV threshold were filtered out in Example III.

Consensus basecalls were determined in an MSA using a pattern classification model that applied an all path probabilistic alignment to assign confidence values to basecalls. For each of the four possible bases ("A", "C", "G", and "T") at each template position, the confidence values from each read at a given location were summed. The summed confidence values were defined as the consensus confidence values, and were correlated with empirical Phred-style empirical quality values (EQV) as shown in FIG. 12. To demonstrate the usefulness of such consensus confidence values, the number of bases in the test data set that were still retained after application of the quality filter was determined. This number was compared with the empirical quality value derived using fold-coverage as the binning method for deriving the EQV. FIG. 13 shows how many basecalls remained when the consensus bases below a given QV threshold were filtered out. When the QV derived by the confidence value defined here was used in a test data set, 70% of the basecalls were selected at QV>~20. In comparison, when the QV was simply derived by binning the bases according the read coverage, 70% of the basecalls were selected at QV>~14, which is much less powerful than the QV assignment using the confidence value described here. The data shown in FIGS. 12 and 13 demonstrated the consensus confidence values defined according to this method were a better predictor of the final quality of the consensus sequence.

Figure 14:
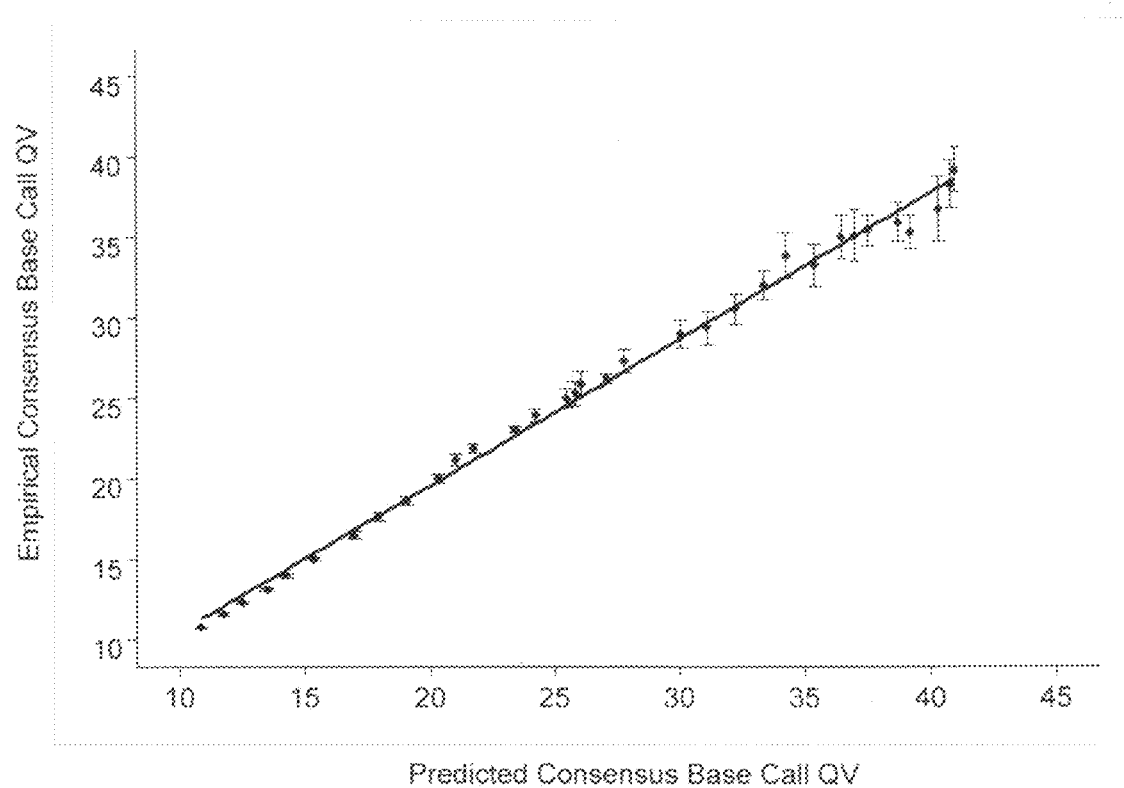
FIG. 14 provides data showing that the prediction of the quality of the resulting consensus base calls agrees well with measured empirical quality values, as described in Example III.

The result of using the confidence value κ defined supra in to predict quality of the resulting consensus base calls. The predictions are compared to the quality values calculated by measured consensus call errors in the test set. FIG. 14 provides data showing that the prediction agrees really well with the measured empirical quality values.

What is claimed is:

1. A method of determining a consensus sequence, comprising:
   a) providing a plurality of replicate sequence reads;
   b) aligning the plurality of replicate sequence reads to generate a multiple sequence alignment;
   c) determining a percent of majority calls for each position in a region of interest in the multiple sequence alignment;
   d) based upon the results of step c, identifying a set of sequential positions in the region of interest, wherein all positions in the set of sequential positions have a percent of majority calls below a threshold; and
   e) using information from the plurality of replicate sequence reads for the set of sequential positions in the region of interest in a pattern classification algorithm to generate a consensus sequence spanning the set of sequential positions, wherein
      a call by the pattern classification algorithm for a first position in the set of sequential positions is dependent upon a call made for a second position in the set of sequential positions that is made by the pattern classification algorithm,
      the first position and the second position are adjacent to each other, and
      at least steps a), b), and e) are performed using a suitably programmed computer.

2. The method of claim 1, wherein the consensus sequence is a polynucleotide sequence.

3. The method of claim 1, wherein the plurality of replicate sequence reads are provided by repeatedly sequencing a single molecule.

4. The method of claim 1, wherein the plurality of replicate sequence reads are provided by simultaneously or sequentially sequencing multiple molecules, each of which comprises at least a portion of said region of interest.

5. The method of claim 1, wherein the percent of majority calls is determined for each position in the region of interest by dividing a count for a most frequent call at a given position by a total number of replicate sequence reads that comprise the given position.

6. The method of claim 1, further comprising generating a path representation of the multiple sequence alignment.

7. The method of claim 6, wherein the path representation is a directed acyclic graph.

8. The method of claim 6, wherein the path representation is subjected to a pruning heuristic.

9. The method of claim 1, wherein the pattern classification algorithm finds a shortest path for calls across the sequential positions.

10. The method of claim 1, wherein the pattern classification algorithm applies a likelihood model.

11. The method of claim 1, wherein the pattern classification algorithm applies an error model.

12. The method of claim 1, wherein the pattern classification algorithm applies a probabilistic graph model.

13. The method of claim 12, wherein the probabilistic graph model comprises an all path probabilistic alignment.

14. The method of claim 1, wherein the pattern classification algorithm applies both a likelihood model and an error model.

15. The method of claim 1, wherein the pattern classification algorithm applies a likelihood model, an error model, and a probabilistic graph model.

16. The method of claim 1, wherein the pattern classification algorithm generates the consensus sequence by maximizing a likelihood based upon the replicate sequence reads.

17. The method of claim 1, wherein the pattern classification algorithm uses a context dependent alignment model parameter based upon a whole genome multiple sequence alignment to generate the consensus sequence.

18. The method of claim 1, wherein the pattern classification algorithm applies a dynamic Bayesian network.

19. The method of claim 18, wherein the dynamic Bayesian network is a Hidden Markov Model.

20. The method of claim 1, further comprising catenating the consensus sequence generated in step e with majority calls from outside the set of sequential positions but in the region of interest.

21. The method of claim 1, wherein multiple sets of sequential positions are identified in step d and multiple consensus sequences for the multiple sets of sequential positions are generated in step e.

22. The method of claim 21, further comprising catenating the multiple consensus sequences with majority calls from outside the multiple sets of sequential positions but in the region of interest to generate a further consensus sequence for the region of interest.

23. The method of claim 21, wherein a first threshold is used to identify at least a first set of sequential positions in the multiple sets of sequential positions and a second threshold is used to identify at least a second set of sequential positions in the multiple sets of sequential positions.

24. The method of claim 1, wherein a set of consensus sequences for the set of sequential positions is generated in step e, further Wherein the set of consensus sequences includes at least a most probable consensus sequence and a second most probable consensus sequence.

25. The method of claim 1 iteratively applied, wherein in a first iteration only a portion of the replicate sequence reads in the plurality of replicate sequence reads is used, and in a subsequent iteration additional sequence reads in the plurality of replicate sequence reads is used.

26. The method of claim 25, wherein in the first iteration only the portion of the replicate sequence reads are aligned in step b, and in the subsequent iteration the additional sequence reads in the plurality of replicate sequence reads are aligned in step b.

27. The method of claim 1 iteratively applied, wherein in a first iteration a first threshold is used to identify a first set of sequential positions, and in a subsequent iteration a second threshold is used to identify a second set of sequential positions, wherein the second threshold identifies fewer sequential positions than the first threshold, thereby causing the first set of sequential positions to have more sequential positions than the second set of sequential positions.

28. A system for determining a consensus sequence, comprising:
   a processor; and
   memory storing an application to be executed by the processor, wherein the application comprises instructions for:
   a) obtaining a plurality of replicate sequence reads;
   b) aligning the plurality of replicate sequence reads to generate a multiple sequence alignment;
   c) determining a percent of majority calls for each position in a region of interest in the multiple sequence alignment;
   d) based upon the results of the determining c), identifying a set of sequential positions in the region of interest, wherein all positions in the set of sequential positions have a percent of majority calls below a threshold; and
   e) using information from the plurality of replicate sequence reads for the set of sequential positions in the region of interest in a pattern classification algorithm to generate a consensus sequence spanning the set of sequential positions, wherein a call by the pattern classification algorithm for a first position in the set of sequential positions is dependent upon a call made for a second position in the set of sequential positions that is made by the pattern classification algorithm, and the first position and the second position are adjacent to each other.

29. A non-transitory computer readable storage medium storing an application to be executed by a processor of a computer, wherein the application is for determining a consensus sequence and wherein the application comprises instructions for:

a) obtaining a plurality of replicate sequence reads;

b) aligning the plurality of replicate sequence reads to generate a multiple sequence alignment;

c) determining a percent of majority calls for each position in a region of interest in the multiple sequence alignment;

d) based upon the results of the determining c), identifying a set of sequential positions in the region of interest, wherein all positions in the set of sequential positions have a percent of majority calls below a threshold; and e) using information from the plurality of replicate sequence reads for the set of sequential positions in the region of interest in a pattern classification algorithm to generate a consensus sequence spanning the set of sequential positions, wherein a call by the pattern classification algorithm for a first position in the set of sequential positions is dependent upon a call made for a second position in the set of sequential positions that is made by the pattern classification algorithm, and the first position and the second position are adjacent to each other.

* * * * *